12) United States Patent
Meyers et al.

US006420153B1

(10) Patent No.: US 6,420,153 B1
(45) Date of Patent: Jul. 16, 2002

(54) 18232, A NOVEL DUAL SPECIFICITY PHOSPHATASE AND USES THEREFOR

(75) Inventors: Rachel A. Meyers, Newton; Nadine Weich, Brookline, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/704,139

(22) Filed: Nov. 1, 2000

Related U.S. Application Data

(60) Provisional application No. 60/185,772, filed on Feb. 29, 2000.

(51) Int. Cl.[7] .............................. C12N 9/16; C12N 1/20; C12N 5/00; C07H 21/02; C07H 21/04
(52) U.S. Cl. ................. 435/196; 435/252.3; 435/320.1; 435/325; 536/23.2; 536/23.1; 536/24.1
(58) Field of Search .............................. 435/196, 252.3, 435/320.1, 325; 536/23.2, 23.1, 24.1

(56) References Cited

FOREIGN PATENT DOCUMENTS

WO       WO 01/12819 A2      2/2001

OTHER PUBLICATIONS

Altschul et al. (1990), J. Mol. Biol., 215:403–410.
Altschul et al. (1997), Nucleic Acids Res., 25(17):3389–3402.
International Human Genome Sequencing Consortium, Initial sequencing and analysis of the human genome, Nature 1, vol. 409, Feb. 15, 2001, www.nature.com.
Barford et al. (1998), Annu. Rev. Biophys. Biomol. Struct., 27:133–64.
Byon et al. (1997), Proc. Soc. Exp. Biol. Med. 216(1):1–20.
Chanda (ed.), Current Protocols in Molecular Biology, 2000, vol. 4, John Wiley & Sons, Inc. (Table of Contents only).
Dahia (2000), Endocr. Relat. Cancer, 7(2):115–129.
Eckstein (2000), Invest. New Drugs, 18(2):149–156.
Fauman et al. (1996), Trends in Biochem 21:413–417.
Karlin et al. (1990), Proc. Natl. Acad. Sci. USA 87(6):2264–2268.
Karlin et al. (1993), Proc. Natl. Acad. Sci. USA 90(12):5873–5877.
Keyse (1995), Biochim. Biophys. Acta 1265:152–160.
Keyse (2000), Curr. Opin. Cell Bio. 12(2)186–192.
Martell et al. (1998), Mol. Cells 8(1):2–11.
Molecular Cloning—A Laboratory Manual, 1989, 2nd Edition, Sambrook et al. (eds.), Cold Spring Harbor Laboratory Press (Table of Contents only).
Myers et al. (1988), CABIOS 4:11–17.
The Human Genome The Sequence of the Human Genome, Science, vol. 291, Feb. 16, 2001 www.sciencemag.org.
Sonnhammer et al. (1997), Proteins 28(3):405–420.

(List continued on next page.)

*Primary Examiner*—Ponnathapu Achutamurthy
*Assistant Examiner*—Yong Pak
(74) *Attorney, Agent, or Firm*—Fish & Richardson P.C.

(57) ABSTRACT

The invention provides isolated nucleic acids molecules, designated 18232 nucleic acid molecules, which encode novel dual specificity phosphatase family members. The invention also provides antisense nucleic acid molecules, recombinant expression vectors containing 18232 nucleic acid molecules, host cells into which the expression vectors have been introduced, and nonhuman transgenic animals in which a 18232 gene has been introduced or disrupted. The invention still further provides isolated 18232 proteins, fusion proteins, antigenic peptides and anti-18232 antibodies. Diagnostic methods utilizing compositions of the invention are also provided. The invention also provides methods of modulating the differentiation and proliferation of hematopoietic cells (e.g., erythroid cells) utilizing the compositions of the invention. Accordingly, methods of treating, preventing and/or diagnosing erythroid-associated disorders such as anemias, leukemias, and erythrocytosis are disclosed.

15 Claims, 8 Drawing Sheets

OTHER PUBLICATIONS

Weintraub et al. (1985), Trends in Genetics, January.
GenBank Accession No. AI040185; Strausberg, Aug. 28, 1998.
GenBank Accession No. AI0106945; Strausberg, Aug. 27, 1998.
GenBank Accession No. AI950221; Strauberg, Mar. 8, 2000.
GenBank Accession No. AI498377, Strausberg, Apr. 14, 1999.
GenBank Accession No. AI018628, Strausberg Jun. 16, 1998.
GenBank Accession No. A W206269, Strausberg, Dec. 2, 1999.
GenBank Accession No. AI672432, Strausberg, Dec. 16, 1999.
GenBank Accession No. AI034374, Strausberg, Jun. 25, 1998.
GenBank Accession No. AA700744, Wilson, Dec. 19, 1997.
GenBank Accession No. AI027213, Strausberg, Aug. 27, 1998.
Klingmuller, Hans (1997), *Eur. J. Chem.* 249:637–647.
Database EMBL Accession No. AA201078, Marra M. et al., Jan. 30, 1997.
Database Swissprot, Accession No. 095147 Yuan L et al., May 1, 1999.

```
                    ┌──── START SEQ ID NO: 1
                    ▼
CCACGCGTCCGGCCCAGTGCCCAGGCCGCGGGGGCGGGGAGGACGGCGCCCGGGGACAGAGAACATGGGACGCAGAGCG
GTCCAAGGCCCCGGCGCCCTGGTGAGGCCCAAACCTCCCGCCATGCCCCGGCCCCAACGAGACCCAAGCCCCCTGTCCC
GGCCCAGCGCCCGCGGGGGACCCAAGCCCCAGCCTGGTCCACCTCGGAGGCCTCTAGGACCCGGGGGCGCCCGGCGGCC
CGCCCGGCTCCCACAAATAGACTCCTGGGCGGGCGCCTGAGCCCCCAAAATAGATCCTCAGGGCCCAAAAGCAGACTCT
                        ┌──── START SEQ ID NO: 2
                        ▼
                        M   G   P   A   E   A   G   R   R   G   A   A   S   P   V   P      16
TCGGCGGGCGCC           ATG GGA CCG GCA GAA GCT GGG CGC CGC GGG GCC GCC TCG CCC GTA CCT      48
            ▲──── START SEQ ID NO: 3
  P   P   L   V   R   V   A   P   S   L   F   L   G   S   A   R   A   A   G   A       36
  CCA CCG TTG GTG CGC GTC GCG CCC TCA CTC TTC CTC GGG AGC GCG CGA GCC GCG GGC GCG       108

E   E   Q   L   A   R   A   G   V   T   L   C   V   N   V   S   R   Q   Q   P       56
  GAG GAG CAG CTG GCG CGC GCG GGA GTC ACG CTG TGC GTC AAC GTC TCC CGC CAG CAG CCC       168

G   P   R   A   P   G   V   A   E   L   R   V   P   V   F   D   D   P   A   E       76
  GGC CCG CGC GCG CCC GGC GTG GCA GAG CTG CGC GTG CCC GTG TTC GAC GAC CCG GCT GAG       228

D   L   L   A   H   L   E   P   T   C   A   A   M   E   A   A   V   R   A   G       96
  GAC CTG CTG GCG CAC CTG GAG CCC ACG TGC GCC GCC ATG GAG GCC GCG GTG CGC GCC GGC       288

G   A   C   L   V   Y   C   K   N   G   R   S   R   S   A   A   V   C   T   A       116
  GGC GCC TGC CTA GTC TAC TGC AAG AAC GGC CGC AGC CGC TCG GCC GCC GTC TGC ACC GCG       348

Y   L   M   R   H   R   G   L   S   L   A   K   A   F   Q   M   V   K   S   A       136
  TAC CTC ATG CGG CAC CGC GGC CTC AGC CTG GCG AAG GCC TTC CAG ATG GTG AAG AGC GCT       408

R   P   V   A   E   P   N   P   G   F   W   S   Q   L   Q   K   Y   E   E   A       156
  CGC CCG GTA GCA GAA CCG AAC CCG GGC TTC TGG TCT CAG CTC CAG AAG TAT GAG GAG GCC       468
                                                        END SEQ ID NO: 2 ────┐
                                                                             ▼
  L   Q   A   Q   S   C   L   Q   G   E   P   P   A   L   G   L   G   P   E   A       176
  CTC CAG GCC CAG TCC TGC CTG CAG GGA GAG CCC CCA GCC TTA GGG TTG GGC CCT GAG GCT       528

*                                                                                    177
  TGA ◄──── END SEQ ID NO: 3                                                           531

AGCTTGAAGGCYTGCTGCCTGGAGGAAGGATGTCCCTGCACTGATACAGAAGCTGTTTCTGGCAAAGCCTGCCGTGTCT
TACATTTGTCTCTCTATCCGGATTAGATGTTGCTATATGAACACATCGGGACTGTGTCTGCAGGAAGGAGCTCCCCATT
CGAGGCCTTCACAGTGTCACCCACATTCACCTCTTTCCACTTAAACGTGTCCCATGAATCTTGTCATAACAGTTTTGTG
TTCCTTAACTATTTTGTCTGCCATGTCATTTATGATGTATATAACCTCTTTAATGCCTGAAATCATAAGAATAATCATC
AAAGGCAAGAGGGTTGTATATTTTCCCGTTGGAGACACATCTGGAATTTGCTGCAATAAAATAATAATAAGAAAGCNNA
AAAAAAAAAAAAAAAAAAAARMAGNAKKCAAAAAKCGAGGKAGAWATRAGCACACCGCTTGTCTTGGGCTGGACATATAA
TTGCTGGCTGGTGGGTTGCAAGAAATTTCTCTTCAAGCATCATCACCCACTTTTGCT ◄──── END SEQ ID NO: 1
```

Fig. 1

```
DSPc: domain 1 of 1, from 18 to 156: score 138.6, E = 1.1e-37
START SEQ ID NO: 4  *———▶ gpseIlphlYLGsystaseanlallkklgIthviNvteevpnpfeld
                          +  +++  p  l+LGs++  a      +++l+   g+t+++Nv++  +p
            18232    18    PLVRVAPSLFLGSARAAG--AEEQLARAGVTLCVNVSRQQPG-----  57 kkndrhytnayisknsgftylqiPnvdDhIYyhiawnhetkiskyfdeav
                           +   +g     l++P  v D         ++ ++++++++ +
            18232    58   ------------PRAPGVAELRVP-VFD--------DPAEDLLAHLEPTC  86 dFIddargqkggkVLVHCqAGiSRSAtliiAYLMktrnlslneAydfvyvY
                          + +++a + gg +LV+C+ G SRSA+++ AYLM+ r+lsl  A+ +v
            18232    87   AAMEAAVRAGGACLVYCKNGRSRSAAVCTAYLMRHRGLSLAKAFQMV---  133 hikerRcpiisPNfgFlrQLieyerk ◀——— * END SEQ ID NO: 4
                          k++R  p    PN+gF+ QL+ ye
            18232   134   --KSAR-PVAEPNPGFWSQLQKYEEA    156
```

Fig. 3A

```
dsp_5: domain 1 of 1, from 18 to 156: score 134.6, E = 1.8e-36
START SEQ ID NO: 5  *———▶ gpseilphlYLGsysdaseanlallkklgIthviNvteevpnnfelk
                          +  +++  p  l+LGs+++a      ++l+   g+t+++Nv++  +p       ++
            18232    18    PLVRVAPSLFLGSARAAG--AEEQLARAGVTLCVNVSRQQP----GP   58 kkndryytneyiskgsgftylqiPnvdDIyyhiawntetkiskyleeave
                          +            +g     l++P+ dD         + ++++++le + +
            18232    59   RA-------------PGVAELRVPVFDD--------PAEDLLAHLEPTCA  87 fIedaekkGGkVLVHCqAGvSRSAtlviAYLMktrnlslrdAydfvyvYh
                          +e+a + gg +LV+C+ G SRSA+++ AYLM+ r+lsl  A+ +v
            18232    88   AMEAAVRAGGACLVYCKNGRSRSAAVCTAYLMRHRGLSLAKAFQMV----  133 ikerRcpiisPNfgFlrQLieyerk ◀——— * END SEQ ID NO: 5
                          k++R  p    PN gF+ QL+ ye
            18232   134   -KSAR-PVAEPNPGFWSQLQKYEEA    156
```

Fig. 3B

SEQUENCE LISTING

```
<160> NUMBER OF SEQ ID NOS:   5

<210> SEQ ID NO 1
<211> LENGTH: 1390
<212> TYPE: DNA
<213> ORGANISM: Homo sapiens
<220> FEATURE:
<221> NAME/KEY: CDS
<222> LOCATION: (329)..(859)
<221> NAME/KEY: misc_feature
<222> LOCATION: (1)..(1390)
<223> OTHER INFORMATION: n = a, t, g, or c

<400> SEQUENCE: 1
ccacgcgtcc ggcccagtgc ccaggccgcg ggggcgggga ggacggcgcc cggggacaga      60
gaacatggga cgcagagcgg tccaaggccc cggcgccctg gtgaggccca aacctcccgc     120
catgccccgg ccccaacgag acccaagccc cctgtcccgg cccagcgccc gcgggggacc     180 caagcccag cctggtccac ctcggaggcc tctaggaccc gggggcgccc ggcggcccgc      240
ccggctccca caaatagact cctgggcggg cgcctgagcc cccaaaatag atcctcaggg    300
cccaaaagca gactcttcgg cgggcgcc atg gga ccg gca gaa gct ggg cgc        352
                                 Met Gly Pro Ala Glu Ala Gly Arg
```

```
cgc ggg gcc gcc tcg ccc gta cct cca ccg ttg gtg cgc gtc gcg ccc      400
Arg Gly Ala Ala Ser Pro Val Pro Pro Pro Leu Val Arg Val Ala Pro
     10              15                  20 tca ctc ttc ctc ggg agc gcg cga gcc gcg ggc gcg gag gag cag ctg      448
Ser Leu Phe Leu Gly Ser Ala Arg Ala Ala Gly Ala Glu Glu Gln Leu
 25              30                  35                      40 gcg cgc gcg gga gtc acg ctg tgc gtc aac gtc tcc cgc cag cag ccc      496
Ala Arg Ala Gly Val Thr Leu Cys Val Asn Val Ser Arg Gln Gln Pro
                 45                  50                  55 ggc ccg cgc gcg ccc ggc gtg gca gag ctg cgc gtg ccc gtg ttc gac      544
Gly Pro Arg Ala Pro Gly Val Ala Glu Leu Arg Val Pro Val Phe Asp
             60                  65                  70 gac ccg gct gag gac ctg ctg gcg cac ctg gag ccc acg tgc gcc gcc      592
Asp Pro Ala Glu Asp Leu Leu Ala His Leu Glu Pro Thr Cys Ala Ala
         75                  80                  85 atg gag gcc gcg gtg cgc gcc ggc ggc gcc tgc cta gtc tac tgc aag      640
Met Glu Ala Ala Val Arg Ala Gly Gly Ala Cys Leu Val Tyr Cys Lys
     90                  95                 100 aac ggc cgc agc cgc tcg gcc gcc gtc tgc acc gcg tac ctc atg cgg      688
Asn Gly Arg Ser Arg Ser Ala Ala Val Cys Thr Ala Tyr Leu Met Arg
105             110                 115                 120 cac cgc ggc ctc agc ctg gcg aag gcc ttc cag atg gtg aag agc gct      736
His Arg Gly Leu Ser Leu Ala Lys Ala Phe Gln Met Val Lys Ser Ala
                125                 130                 135 cgc ccg gta gca gaa ccg aac ccg ggc ttc tgg tct cag ctc cag aag      784
Arg Pro Val Ala Glu Pro Asn Pro Gly Phe Trp Ser Gln Leu Gln Lys
            140                 145                 150 tat gag gag gcc ctc cag gcc cag tcc tgc ctg cag gga gag ccc cca      832
Tyr Glu Glu Ala Leu Gln Ala Gln Ser Cys Leu Gln Gly Glu Pro Pro
        155                 160                 165 gcc tta ggg ttg ggc cct gag gct tga agcttgaagg cytgctgcct            879
Ala Leu Gly Leu Gly Pro Glu Ala
    170                 175 ggaggaagga tgtccctgca ctgatacaga agctgtttct ggcaaagcct gccgtgtctt    939
acatttgtct ctctatccgg attagatgtt gctatatgaa cacatcggga ctgtgtctgc    999
aggaaggagc tccccattcg aggccttcac agtgtcaccc acattcacct ctttccactt   1059
aaacgtgtcc catgaatctt gtcataacag ttttgtgttc cttaactatt tgtctgcca    1119 tgtcatttat gatgtatata acctctttaa tgcctgaaat cataagaata atcatcaaag   1179
gcaagagggt tgtatatttt cccgttggag acacatctgg aatttgctgc aataaaataa   1239
taataagaaa gcnnaaaaaa aaaaaaaaaa aaaarmagna kkcaaaaakc gaggkagawa   1299
tragcacacc gcttgtcttg ggctggacat ataattgctg gctggtgggt tgcaagaaat   1359
ttctcttcaa gcatcatcac ccacttttgc t                                 1390

<210> SEQ ID NO 2
<211> LENGTH: 176
<212> TYPE: PRT
<213> ORGANISM: Homo sapiens
<220> FEATURE:
<221> NAME/KEY: misc_feature
<222> LOCATION: (1)..(1390)
<223> OTHER INFORMATION: n = a, t, g, or c

<400> SEQUENCE: 2

Met Gly Pro Ala Glu Ala Gly Arg Arg Gly Ala Ala Ser Pro Val Pro
1               5                   10                  15
```

```
Pro Pro Leu Val Arg Val Ala Pro Ser Leu Phe Leu Gly Ser Ala Arg
            20                  25                  30

Ala Ala Gly Ala Glu Glu Gln Leu Ala Arg Ala Gly Val Thr Leu Cys
        35                  40                  45

Val Asn Val Ser Arg Gln Gln Pro Gly Pro Arg Ala Pro Gly Val Ala
    50                  55                  60

Glu Leu Arg Val Pro Val Phe Asp Asp Pro Ala Glu Asp Leu Leu Ala
65              70                  75                  80

His Leu Glu Pro Thr Cys Ala Ala Met Glu Ala Val Arg Ala Gly
                85                  90                  95

Gly Ala Cys Leu Val Tyr Cys Lys Asn Gly Arg Ser Arg Ser Ala Ala
            100                 105                 110

Val Cys Thr Ala Tyr Leu Met Arg His Arg Gly Leu Ser Leu Ala Lys
        115                 120                 125

Ala Phe Gln Met Val Lys Ser Ala Arg Pro Val Ala Glu Pro Asn Pro
    130                 135                 140

Gly Phe Trp Ser Gln Leu Gln Lys Tyr Glu Glu Ala Leu Gln Ala Gln
145                 150                 155                 160

Ser Cys Leu Gln Gly Glu Pro Pro Ala Leu Gly Leu Gly Pro Glu Ala
                165                 170                 175

<210> SEQ ID NO 3
<211> LENGTH: 531
<212> TYPE: DNA
<213> ORGANISM: Homo sapiens

<400> SEQUENCE: 3
atgggaccgg cagaagctgg gcgccgcggg gccgcctcgc ccgtacctcc accgttggtg    60
cgcgtcgcgc cctcactctt cctcgggagc gcgcgagccg cgggcgcgga ggagcagctg   120
gcgcgcgcgg gagtcacgct gtgcgtcaac gtctcccgcc agcagcccgg ccgcgcgcg    180 cccggcgtgg cagagctgcg cgtgcccgtg ttcgacgacc cggctgagga cctgctggcg   240
cacctggagc ccacgtgcgc cgccatggag gcgcgggtgc gcgccggcgg cgcctgccta   300
gtctactgca agaacggccg cagccgctcg gccgccgtct gcaccgcgta cctcatgcgg   360
caccgcggcc tcagcctggc gaaggccttc agatggtga agagcgctcg cccggtagca   420
gaaccgaacc cgggcttctg gtctcagctc cagaagtatg aggaggccct ccaggcccag   480
tcctgcctgc agggagagcc cccagcctta gggttgggcc ctgaggcttg a            531

<210> SEQ ID NO 4
<211> LENGTH: 173
<212> TYPE: PRT
<213> ORGANISM: Artificial/Unknown
<220> FEATURE:
<221> NAME/KEY: VARIANT
<222> LOCATION: (1)..(173)
<223> OTHER INFORMATION: consensus sequence

<400> SEQUENCE: 4

Gly Pro Ser Glu Ile Leu Pro His Leu Tyr Leu Gly Ser Tyr Ser Thr
1               5                   10                  15

Ala Ser Glu Ala Asn Leu Ala Leu Leu Lys Lys Leu Gly Ile Thr His
            20                  25                  30

Val Ile Asn Val Thr Glu Glu Val Pro Asn Pro Phe Glu Leu Asp Lys
        35                  40                  45

Lys Asn Asp Arg His Tyr Thr Asn Ala Tyr Ile Ser Lys Asn Ser Gly
    50                  55                  60
```

-continued

```
Phe Thr Tyr Leu Gln Ile Pro Asn Val Asp Asp His Ile Tyr Tyr His
 65                  70                  75                  80

Ile Ala Trp Asn His Glu Thr Lys Ile Ser Lys Tyr Phe Asp Glu Ala
                 85                  90                  95

Val Asp Phe Ile Asp Asp Ala Arg Gln Lys Gly Gly Lys Val Leu Val
                100                 105                 110

His Cys Gln Ala Gly Ile Ser Arg Ser Ala Thr Leu Ile Ile Ala Tyr
                115                 120                 125

Leu Met Lys Thr Arg Asn Leu Ser Leu Asn Glu Ala Tyr Asp Phe Val
                130                 135                 140

Tyr Val Tyr His Ile Lys Glu Arg Arg Cys Pro Ile Ile Ser Pro Asn
145                 150                 155                 160

Phe Gly Phe Leu Arg Gln Leu Ile Glu Tyr Glu Arg Lys
                165                 170
```

<210> SEQ ID NO 5
<211> LENGTH: 172
<212> TYPE: PRT
<213> ORGANISM: Artificial/Unknown
<220> FEATURE:
<221> NAME/KEY: VARIANT
<222> LOCATION: (1)..(172)
<223> OTHER INFORMATION: consensus sequence

<400> SEQUENCE: 5

```
Gly Pro Ser Glu Ile Leu Pro His Leu Tyr Leu Gly Ser Tyr Ser Asp
  1               5                  10                  15

Ala Ser Glu Ala Asn Leu Ala Leu Leu Lys Lys Leu Gly Ile Thr His
                 20                  25                  30

Val Ile Asn Val Thr Glu Glu Val Pro Asn Asn Phe Glu Leu Lys Lys
                 35                  40                  45

Lys Asn Asp Arg Tyr Tyr Thr Asn Glu Tyr Ile Ser Lys Gly Ser Gly
                 50                  55                  60

Phe Thr Tyr Leu Gln Ile Pro Asn Val Asp Asp Ile Tyr Tyr His Ile
 65                  70                  75                  80

Ala Trp Asn Thr Glu Thr Lys Ile Ser Lys Tyr Leu Glu Glu Ala Val
                 85                  90                  95

Glu Phe Ile Glu Asp Ala Glu Lys Lys Gly Gly Lys Val Leu Val His
                100                 105                 110

Cys Gln Ala Gly Val Ser Arg Ser Ala Thr Leu Val Ile Ala Tyr Leu
                115                 120                 125

Met Lys Thr Arg Asn Leu Ser Leu Arg Asp Ala Tyr Asp Phe Val Tyr
                130                 135                 140

Val Tyr His Ile Lys Glu Arg Arg Cys Pro Ile Ile Ser Pro Asn Phe
145                 150                 155                 160

Gly Phe Leu Arg Gln Leu Ile Glu Tyr Glu Arg Lys
                165                 170
```

18232, A NOVEL DUAL SPECIFICITY PHOSPHATASE AND USES THEREFOR

RELATED APPLICATIONS

This application claims priority to U.S. provisional application No. 60/185,772 filed on Feb. 29, 2000, the contents of which are incorporated herein by reference.

BACKGROUND OF THE INVENTION

The intracellular phosphorylation of proteins is critical for a plethora of regulatory and signalling mechanisms in eukaryotic cells. Phosphorylation events can govern a wide range of cellular processes, including cell proliferation, differentiation, transcription, and morphology. Serine/threonine protein kinases, also called serine protein kinases, are frequently utilized in signalling cascades as the activity of these enzymes can be finely regulated by stimuli. A common stimulus is phosphorylation of the serine protein kinase itself. Hence, signalling pathways, such as the MAP protein kinase cascade and the JAK/STAT pathway, can contain multiple proteins kinases which are sequentially activated. Ultimately, kinase cascades can result in the phosphorylation of cytoskeletal proteins, transcription factors, and biosynthetic enzymes. Another class of kinases includes the receptor tyrosine kinases. Activated receptor tyrosine kinases not only autophosphorylate, but phosphorylate other intracellular signalling molecules, including those specifically bound to autophosphorylated receptors.

An essential component of the aforementioned signalling pathways is the ability of the cell to desensitize, recycle, and counteract phosphorylation signals. The cell primarily utilizes enzymes, termed phosphatases, which remove the phosphate on tyrosine, serine, and threonine side chains. Dual specificity phosphatases hydrolyze phosphotyrosine, phosphothreonine, and phosphoserine residues (for a review, see, e.g., Fauman and Saper (1996) *Trends in Biochem.* 21:412). This class of proteins is exemplified by the VH1 or vaccinia virus late H1 gene protein, whose catalytic activity is required for vaccinia virus replication. A human homolog of VH1, VHR, has also been identified. VH1-like dual specificity phosphatase can also include the phosphatases PAC-1 and CL100/MKP-1, hVH-2/MKP-2, hVH-3, MKP-3, MKP-X, MKP-4, hVH-5, and M3/6 proteins. The PAC-1 and CL100 proteins hydrolyze phosphothreonine and phosphotyrosine residues on phosphorylated MAP (mitogen activated protein) kinases. In order to modulate signalling events, the activity and expression of dual specificity phosphatases can be finely regulated. For example, the PAC-1 and CL100 phosphatase can be induced by growth factors (Keyse, S (1995) *Biochim. Biophys. Acta* 1265:152–160).

Thus, the function of dual specificity phosphatase proteins can be critical for the regulation of cellular processes such as proliferation and differentiation. Given the important biological roles and properties of such phosphatases, there exists a need for the identification of novel genes encoding such proteins as well as for the discovery of modulators of such molecules for use in regulating a variety of normal and/or pathological cellular processes.

SUMMARY OF THE INVENTION

The present invention is based, in part, on the discovery of a novel dual specificity phosphatase, referred to herein as "18232" nucleic acid and protein molecules. The nucleotide sequence of a cDNA encoding 18232 is shown in SEQ ID NO:1, and the amino acid sequence of a 18232 polypeptide is shown in SEQ ID NO:2. In addition, the nucleotide sequence of the coding region is depicted in SEQ ID NO:3.

Accordingly, in one aspect, the invention features a nucleic acid molecule that encodes a 18232 protein or polypeptide, e.g., a biologically active portion of the 18232 protein. In a preferred embodiment, the isolated nucleic acid molecule encodes a polypeptide having the amino acid sequence of SEQ ID NO:2. In other embodiments, the invention provides isolated 18232 nucleic acid molecules having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule that hybridizes under stringent hybridization conditions to a nucleic acid molecule comprising the nucleotide sequence of SEQ ID NO:1 or 3, wherein the nucleic acid encodes a full length 18232 protein or an active fragment thereof.

In a related aspect, the invention further provides nucleic acid constructs that include a 18232 nucleic acid molecule described herein. In certain embodiments, the nucleic acid molecules of the invention are operatively linked to native or heterologous regulatory sequences. Also included are vectors and host cells containing the 18232 nucleic acid molecules of the invention, e.g., vectors and host cells suitable for producing 18232 nucleic acid molecules and polypeptides.

In another related aspect, the invention provides nucleic acid fragments suitable as primers or hybridization probes for the detection of 18232-encoding nucleic acids.

In still another related aspect, isolated nucleic acid molecules that are antisense to a 18232 encoding nucleic acid molecule are provided.

In another aspect, the invention features 18232 polypeptides and biologically active or antigenic fragments thereof that are useful, e.g., as reagents or targets in assays applicable to treatment and diagnosis of 18232-mediated or related disorders. In another embodiment, the invention provides 18232 polypeptides having a 18232 activity. Preferred polypeptides are 18232 proteins including at least one dual specificity phosphatase catalytic domain, and, preferably, having a 18232 activity, e.g., a 18232 activity as described herein.

In other embodiments, the invention provides 18232 polypeptides, e.g., a 18232 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence that hybridizes under stringent hybridization conditions to a nucleic acid molecule comprising the nucleotide sequence of SEQ ID NO:1 or 3, wherein the nucleic acid encodes a full length 18232 protein or an active fragment thereof.

In a related aspect, the invention provides 18232 polypeptides or fragments operatively linked to non-18232 polypeptides to form fusion proteins.

In another aspect, the invention features antibodies and antigen-binding fragments thereof, that react with, or more preferably specifically bind 18232 polypeptides.

In another aspect, the invention provides methods of screening for compounds that modulate the expression or activity of the 18232 polypeptides or nucleic acids.

In still another aspect, the invention provides a process for modulating 18232 polypeptide or nucleic acid expression or activity, e.g. using the screened compounds. In certain embodiments, the methods involve treatment of conditions related to decreased activity or expression of the 18232 polypeptides or nucleic acids, such as conditions involving aberrant cellular proliferation of a 18232 expressing cell, e.g., a hematopoietic cell (e.g., an erythroid cell (e.g., an erythrocyte or an erythroblast), a CD34 positive cell, a glycophorin A-expressing cell, a megakaryocyte). The condition may involve increased hematopoietic cell activity or proliferation as in the case of leukemia, e.g., an erythroleukemia; or decreased hematopoietic cell differentiation as in the case of, e.g., an anemia.

In still another aspect, the invention features a method of modulating (e.g., enhancing or inhibiting) the proliferation, survival, and/or differentiation of a cell, e.g., a 18232-expressing cell, e.g., a hematopoietic cell (e.g., an erythroid cell, a bone marrow cell such as a CD34 positive cell, a megakaryocyte). The method includes contacting the cell with an agent that modulates the activity or expression of a 18232 polypeptide or nucleic acid, in an amount effective to modulate the proliferation and/or differentiation of the cell.

In a preferred embodiment, the 18232 polypeptide has an amino acid sequence identical to, or substantially identical to, SEQ ID NO:2. In other embodiments, the 18232 polypeptide is a fragment of at least 15, 20, 50, 100, 150, or more contiguous amino acids of SEQ ID NO:2.

In a preferred embodiment, the 18232 nucleic acid has a nucleotide sequence identical to, or substantially identical to, SEQ ID NO:1 or 3. In other embodiments, the 18232 nucleic acid is a fragment of at least 50, 100, 150, 200, 250, 300, 350, 400, 450, 500, or more contiguous nucleotides of SEQ ID NO:1 or 3.

In a preferred embodiment, the agent modulates (e.g., increases or decreases) protein phosphatase activity.

In a preferred embodiment, the agent modulates (e.g., increases or decreases) expression of the 18232 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or an 18232 nucleic acid, or any combination thereof.

In a preferred embodiment, the agent is administered in combination with a cytotoxic agent.

In a preferred embodiment, the cell, e.g., the 18232-expressing cell, is a hematopoietic cell, e.g., a myeloid, lymphoid or erythroid cell, or a precursor cell thereof Examples of such cells include myelocytic cells (polymorphonuclear cells), erythrocytic cells, lymphocytes, monocytes, reticular cells, plasma cells and megakaryocytes, as well as stem cells for the different lineages, and precursors for the committed progenitor cells, for example, precursors of blood cells (e.g., red blood cells, such as erythroblasts), macrophages (monoblasts), platelets (megakaryocytes), polymorphonuclear leucocytes (myeloblasts), and lymphocytes (lymphoblasts).

In a preferred embodiment, the cell, e.g., the 18232-expressing cell, is a bone marrow cell, e.g., a bone marrow CD34-expressing cell. Examples of CD34-expressing cells include immature hematopoietic precursor cells, hematopoietic colony-forming cells in bone marrow, including unipotent (CFU-GM, BFU-E) and pluripotent progenitors (CFU-GEMM, CFU-Mix and CFU-blast); as well as stromal cell precursors, terminal deoxynucleotidyl transferase (TdT) expressing B- and T-lymphoid precursors, early myeloid cells and early erythroid cells.

In a preferred embodiment, the cell, e.g., the 18232-expressing cell, is a bone marrow erythroid cell, e.g., an erythroid progenitor (e.g., a glycophorin A expressing cell) or a differentiated cell, e.g., an erythrocyte or a megakaryocyte.

In one embodiment, the hematopoietic cell is a lymphoid cell, e.g., B cells, and their precursors, T cells (e.g., $CD4^+8^+$ T cells, $CD4^+8^-$ T cells (e.g., helper T cells), $CD4^-CD8^+$ T cells (e.g., cytotoxic T cells), $CD4^-8^-$ T cells, and natural killer T cells) and their precursors.

In a preferred embodiment, the cell, e.g., the 18232-expressing cell, is further contacted with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin. Most preferably, the protein is erythropoietin. The protein contacting step can occur before, at the same time, or after the agent is contacted. The protein contacting step can be effected in vitro or ex vivo. For example, the cell, e.g., the 18232-expressing cell is obtained from a subject, e.g., a patient, and contacted with the protein ex vivo. The treated cell can be re-introduced into the subject. Alternatively, the protein contacting step can occur in vivo.

In a preferred embodiment, the agent and the 18232-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with an erythroid-associated disorder. For example, the subject can be a patient with an anemia, e.g., hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Alternatively, the subject can be a cancer patient, e.g., a patient with leukemic cancer, e.g., an erythroid leukemia, or a carcinoma, e.g., a renal carcinoma. In other embodiments, the subject is a non-human animal, e.g., an experimental animal.

The contacting step(s) can be repeated.

In a preferred embodiment, the agent decreases the proliferation and/or enhances the differentiation of the cell, e.g., the 18232-expressing cell, e.g., the erythroid cell. Such agents can be used to treat or prevent cancers, e.g., leukemic cancers such as erythroid leukemias, or carcinomas, e.g., renal or lung carcinomas.

In a preferred embodiment, the agent increases the number of erythroid cells, by e.g., increasing the proliferation, survival, and/or stimulating the differentiation, of erythroid progenitor cells. Such agents can be used to treat or prevent anemias, e.g., hemolytic anemias, aberrant erythropoiesis, secondary anemias in non-hematolic disorders, anemias of chronic diseases such as chronic renal failure; endocrine deficiency diseases; and/or erythrocytosis (e.g., polycythemias).

In a preferred embodiment, the agent increases the number of erythroid cells, by e.g., increasing the proliferation, survival, and/or stimulating the differentiation, of granulocytic and monocytic progenitor cells, e.g., CFU-GM, CFU-G (colony forming unit—granulocyte), myeloblast, promyelocyte, myelocyte, a metamyelocyte, or a band cell.

Such compounds can be used to treat or prevent neutropenia and granulocytopenia, e.g., conditions caused by cytotoxic chemotherapy, AIDS, congenital and cyclic neutropenia, myelodysplastic syndromes, or aplastic anemia.

In another aspect, the invention features a method of modulating hematopoiesis, e.g., erythropoiesis, comprising contacting a hematopoietic cell, e.g., a blood cell, such as an erythroid cell, with a agent that increases or decreases the activity or expression of a 18232 polypeptide or nucleic acid, thereby modulating the differentiation of the hematopoietic cell, e.g., the blood cell.

In a preferred embodiment, the 18232 polypeptide has an amino acid sequence identical to, or substantially identical to, SEQ ID NO:2. In other embodiments, the 18232 polypeptide is a fragment of at least 15, 20, 50, 100, 150, or more contiguous amino acids of SEQ ID NO:2.

In a preferred embodiment, the 18232 nucleic acid has a nucleotide sequence identical to, or substantially identical to, SEQ ID NO:1 or 3. In other embodiments, the 18232 nucleic acid is a fragment of at least 50, 100, 150, 200, 250, 300, 350, 400, 450, 500, or more contiguous nucleotides of SEQ ID NO:1 or 3.

In a preferred embodiment, the agent modulates (e.g., increases or decreases) protein phosphatase activity.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or an 18232 nucleic acid, or any combination thereof.

In a preferred embodiment, the agent is administered in combination with a cytotoxic agent.

In a preferred embodiment, the hematopoietic cell is an erythroid cell, e.g., an erythroid progenitor or differentiated cell, e.g., an erythrocyte or a megakaryocyte.

In a preferred embodiment, the hematopoietic cell is a bone marrow CD34-expressing cell.

In a preferred embodiment, the agent and the 18232-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with a hematopoietic disorder such as an erythroid-associated disorder. For example, the subject can be a patient with an anemia, e.g., a drug-induced anemia (e.g., a chemotherapy-induced anemia), hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Preferably, the erythroid-associated disorder is a drug-induced anemia (e.g., a chemotherapy induced anemia). Alternatively, the subject can be a cancer patient, e.g., a patient with leukemic cancer, e.g., an erythroid leukemia. In other embodiments, the subject is a non-human animal, e.g., an experimental animal.

In a preferred embodiment, the method further includes contacting of the erythroid cell with a protein, e.g., a hormone. The protein can be a member of the following non-limiting group: G-CSF, GM-CSF, stem cell factor, interleukin-3 (IL-3), IL-4, Flt-3 ligand, thrombopoietin, and erythropoietin. More preferably, the protein is erythropoietin. The protein contacting step can occur before, at the same time, or after the agent is contacted. The protein contacting step can be effected in vitro or ex vivo. For example, the cell, e.g., the erythroid cell can be obtained from a subject, e.g., a patient, and contacted with the protein ex vivo. The treated cell can be re-introduced into the subject. Alternatively, the protein contacting step can occur in vivo.

The contacting step(s) can be repeated.

In a preferred embodiment, the agent increases the number of hematopoietic cells, e.g., erythroid cells, by e.g., increasing the proliferation, survival, and/or stimulating the differentiation, of hematopoietic (e.g., erythroid) progenitor cells, in the subject. Such agents can be used to treat an anemia, e.g., a drug-(e.g., chemotherapy-) induced anemia, hemolytic anemia, aberrant erythropoiesis, secondary anemia in non-hematolic disorder, anemia of chronic diseases such as chronic renal failure; endocrine deficiency disease; and/or erythrocytosis (e.g., polycythemias).

In a preferred embodiment, the agent increases the number of erythroid cells, by e.g., increasing the proliferation, survival, and/or stimulating the differentiation, of granulocytic and monocytic progenitor cells, e.g., CFU-GM, CFU-G (colony forming unit—granulocyte), myeloblast, promyelocyte, myelocyte, a metamyelocyte, or a band cell. Such compounds can be used to treat or prevent neutropenia and granulocytopenia, e.g., conditions caused by cytotoxic chemotherapy, AIDS, congenital and cyclic neutropenia, myelodysplastic syndromes, or aplastic anemia.

In yet another aspect, the invention features a method of treating or preventing a hematopoietic disorder, e.g., an erythroid-associated disorder, in a subject. The method includes administering to the subject an effective amount of an agent that modulates the activity or expression of a 18232 polypeptide or nucleic acid such that the hematopoietic disorder is ameliorated or prevented.

In a preferred embodiment, the 18232 polypeptide has an amino acid sequence identical to, or substantially identical to, SEQ ID NO:2. In other embodiments, the 18232 polypeptide is a fragment of at least 15, 20, 50, 100, 150, or more contiguous amino acids of SEQ ID NO:2.

In a preferred embodiment, the 18232 nucleic acid has a nucleotide sequence identical to, or substantially identical to, SEQ ID NO:1 or 3. In other embodiments, the 18232 nucleic acid is a fragment of at least 50, 100, 150, 200, 250, 300, 350, 400, 450, 500, or more contiguous nucleotides of SEQ ID NO:1 or 3.

In a preferred embodiment, the agent modulates (e.g., increases or decreases) protein phosphatase activity.

In a preferred embodiment, the agent modulates (e.g., increases or decreases) expression of the 18232 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or an 18232 nucleic acid, or any combination thereof.

In a preferred embodiment, the agent is administered in combination with a cytotoxic agent.

In a preferred embodiment, the subject is a human, e.g., a patient with a hematopoietic disorder, e.g., an erythroid-associated disorder. For example, the subject can be a patient with an anemia, e.g., a drug-(chemotherapy-) induced anemia, hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Preferably, the anemia is a drug-(chemotherapy-) induced anemia. Alternatively, the subject can be a cancer patient, e.g., a patient with leukemic cancer, e.g., an erythroid leukemia, or a patient with a carcinoma, e.g., a renal carcinoma. In other embodiments, the subject is a non-human animal, e.g., an experimental animal.

In a preferred embodiment, the agent decreases the proliferation and/or enhances the differentiation of a cell, e.g., a 18232-expressing cell, e.g., a hematopoietic cell (e.g., an erythroid cell), in the subject. Such agents can be used to treat or prevent cancers, e.g., leukemic cancers such as erythroid leukemias, or carcinomas, e.g., renal carcinomas.

In a preferred embodiment, the agent increases the number of hematopoietic cells, e.g., blood cells (e.g., erythroid cells), by e.g., increasing the proliferation, and/or stimulating the differentiation, of erythroid progenitor cells, in the subject. Such agents can be used to treat an anemia, e.g., a drug-(chemotherapy-) induced anemia, a hemolytic anemia, aberrant erythropoiesis, a secondary anemia in non-hematolic disorder, anemia of chronic diseases such as chronic renal failure; endocrine deficiency disease; and/or erythrocytosis (e.g., polycythemias).

In a preferred embodiment, the agent increases the number of erythroid cells, by e.g., increasing the proliferation, survival, and/or stimulating the differentiation, of granulocytic and monocytic progenitor cells, e.g., CFU-GM, CFU-G (colony forming unit—granulocyte), myeloblast, promyelocyte, myelocyte, a metamyelocyte, or a band cell. Such compounds can be used to treat or prevent neutropenia and granulocytopenia, e.g., conditions caused by cytotoxic chemotherapy, AIDS, congenital and cyclic neutropenia, myelodysplastic syndromes, or aplastic anemia.

In a preferred embodiment, the disorder is a hematopoietic disorder, e.g. an erythroid-associated disorder. Examples of erythroid-associated disorder include drug-(chemotherapy-) induced anemia, hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Preferably, the erythroid associated disorder is a drug-(chemotherapy-) induced anemia.

In a preferred embodiment, the disorder is a cancer, e.g., a leukemic cancer, e.g., an erythroid leukemia, or a carcinoma, e.g., a renal carcinoma.

In a preferred embodiment, the method further includes administering an effective amount of a protein, e.g., a cytokine or a hormone, to the subject. Exemplary proteins include, but are not limited to, G-CSF, GM-CSF, stem cell factor, interleukin-3 (IL-3), IL-4, Flt-3 ligand, thrombopoietin, and erythropoietin. Preferably, the protein is erythropoietin. The protein can be administered before, at the same time or after, administration of the agent.

The administration of the agent and/or protein can be repeated.

In still another aspect, the invention features a method for evaluating the efficacy of a treatment of a disorder, in a subject. The method includes treating a subject with a protocol under evaluation; assessing the expression of a 18232 nucleic acid or 18232 polypeptide, such that a change in the level of 18232 nucleic acid or 18232 polypeptide after treatment, relative to the level before treatment, is indicative of the efficacy of the treatment of the disorder.

In a preferred embodiment, the disorder is a hematopoietic disorder, e.g., an erythroid-associated disorder. Examples of erythroid-associated disorders include an anemia, e.g., a drug-(e.g., chemotherapy-) induced anemia, a hemolytic anemia, aberrant erythropoiesis, secondary anemia in non-hematolic disorder, anemias of chronic disease such as chronic renal failure; endocrine deficiency diseases; and/or erythrocytosis (e.g., polycythemia).

In a preferred embodiment, the disorder is a cancer, e.g., leukemic cancer, e.g., an erythroid leukemia, or a carcinoma, e.g., a renal carcinoma.

In a preferred embodiment, the subject is a human.

In a preferred embodiment, the subject is an experimental animal, e.g., an animal model for a hematopoietic-(e.g., an erythroid-) associated disorder.

In a preferred embodiment, the method can further include treating the subject with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin. Preferably, the protein is erythropoietin.

The invention also features a method of diagnosing a disorder, e.g., hematopoietic disorder (e.g., an erythroid-associated disorder), in a subject. The method includes evaluating the expression or activity of a 18232 nucleic acid or a 18232 polypeptide, such that, a difference in the level of 18232 nucleic acid or 18232 polypeptide relative to a normal subject or a cohort of normal subjects is indicative of the disorder.

In a preferred embodiment, the subject is a human.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 18232 nucleic acid or polypeptide, such that a signal is generated relative to the level of activity or expression of the 18232 nucleic acid or polypeptide.

In a preferred embodiment, the disorder is a hematopoietic disorder, e.g., a hematopoietic disorder as described herein.

In a preferred embodiment, the disorder is an erythroid-associated disorder, e.g., an erythroid-associated disorder as described herein.

The invention also provides assays for determining the activity of or the presence or absence of 18232 polypeptides or nucleic acid molecules in a biological sample, including for disease diagnosis.

In further aspect, the invention provides assays for determining the presence or absence of a genetic alteration in a 18232 polypeptide or nucleic acid molecule, including for disease diagnosis.

In yet another aspect, the invention features a method for identifying an agent, e.g., a compound, which modulates the activity of a 18232 polypeptide, e.g., a 18232 polypeptide as described herein, or the expression of a 18232 nucleic acid, e.g., a 18232 nucleic acid as described herein, including contacting the 18232 polypeptide or nucleic acid with a test agent (e.g., a test compound); and determining the effect of the test compound on the activity of the polypeptide or nucleic acid to thereby identify a compound which modulates the activity of the polypeptide or nucleic acid.

In a preferred embodiment, the activity of the 18232 polypeptide is a protein phosphatase activity.

In a preferred embodiment, the activity of the 18232 polypeptide is hematopoiesis, e.g., erythropoiesis.

In a preferred embodiment, the activity of the 18232 polypeptide is proliferation, differentiation, and/or survival of a cell, e.g., a 18232-expressing cell, e.g., a hematopoietic cell (e.g., a bone marrow cell such as a CD34 positive cell, an erythroid cell, a megakaryocyte).

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or an 18232 nucleic acid, or any combination thereof.

Other features and advantages of the invention will be apparent from the following detailed description, and from the claims.

BRIEF DESCRIPTION OF THE DRAWINGS

FIG. 1 depicts a cDNA sequence (SEQ ID NO:1) and predicted amino acid sequence (SEQ ID NO:2) of human 18232. The methionine-initiated open reading frame of human 18232 (without the 5' and 3' untranslated regions) starts at nucleotide 329 and ends at nucleotide 859 of SEQ ID NO:1 (shown also as coding sequence (SEQ ID NO:3)).

FIGS. 3A and 3B depict alignments of dual specificity phosphatase catalytic domains (DSPc and dsp_5, respectively) and of human 18232 amino acid sequence with a consensus amino acid sequence derived from a hidden Markov model using PFAM (FIG. 3A) and SMART (FIG. 3B). The upper sequence is the consensus amino acid sequence (SEQ ID NOs:4 and 5, respectively), while the lower amino acid sequence corresponds to amino acids 18 to 156 of SEQ ID NO:2.

DETAILED DESCRIPTION

Figure 2:
FIG. 2 depicts a hydropathy plot of human 18232. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 18232 are indicated.
Figure 4:
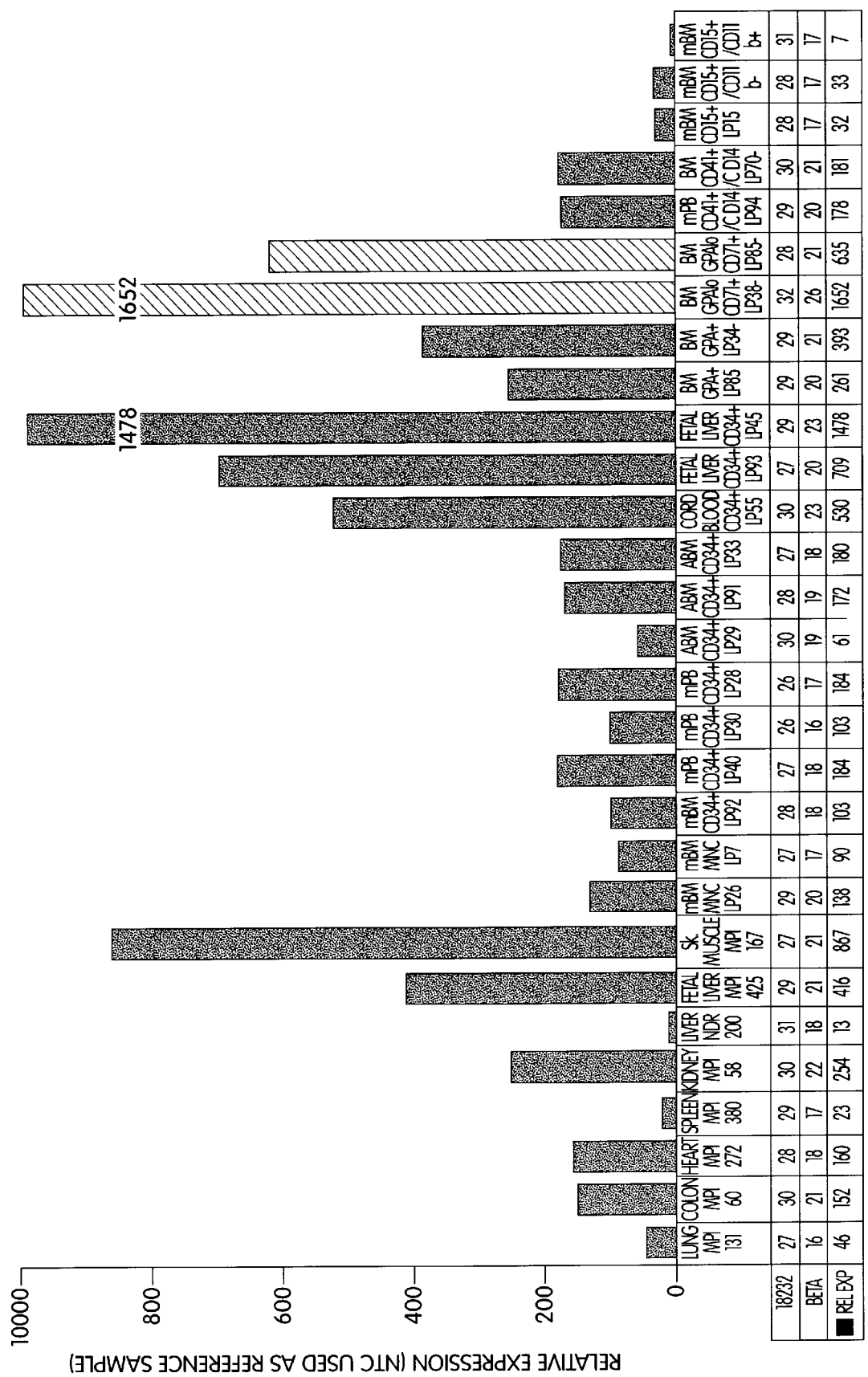
FIG. 4 is a bar graph depicting relative 18232 mRNA expression as determined by TaqMan assays on mRNA derived from the human lung, colon, bone marrow cells (e.g., bone marrow glycophorin A (GPA)-expressing cells), peripheral blood cells, cord blood, and fetal liver. The highest 18232 mRNA expression, i.e., greater than 450 relative units, was observed in skeletal muscle, cord blood (CD34+ cells), fetal liver (CD34+ cells), and bone marrow with low GPA levels and CD71 positive (BM GAPlo CD71+).

The human 18232 sequence (FIG. 1; SEQ ID NO:1), which is approximately 1390 nucleotides long including untranslated regions, contains a predicted methionine-initiated coding sequence of about 531 nucleotides (nucleotides 329 to 859 of SEQ ID NO:1; SEQ ID NO:3). The coding sequence encodes a 176 amino acid protein (SEQ ID NO:2).

Human 18232 contains the following regions or other structural features:

a dual specificity phosphatase, catalytic domain (PF00782) located from about amino acid residue 18 to 156 of SEQ ID NO:2;

a "C—$X_5$—R" motif, located at about amino acid residues 103 to 109 of SEQ ID NO:2, including an active site cysteine at about amino acid 103 of SEQ ID NO:2, and an active site arginine at about amino acid 109 of SEQ ID NO:2;

a VH1-like dual specificity phosphatase loop located at about amino acid residues 70 to 74 of SEQ ID NO:2, including a conserved general acid, aspartic acid at about residue 74 of SEQ ID NO:2;

one predicted N-glycosylation site (PS00001) at amino acids 50 to 53;

Protein Kinase C sites (PS00005) at about amino acids 30 to 32 and 135 to 137 of SEQ ID NO:2;

three predicted N-myristylation sites (PS00008) from about amino acid 29 to 34, 44 to 49, and 123 to 128 of SEQ ID NO:2; and one amidation site (PS00009) at amino acids 6 to 9 of SEQ ID NO:2.

For general information regarding PFAM identifiers, PS prefix and PF prefix domain identification numbers, refer to Sonnhammer et al. (1997) *Protein* 28:405-420.

The 18232 protein contains a significant number of structural characteristics in common with members of the dual specificity phosphatase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Dual specificity phosphatase proteins are characterized by a common fold. Examples of members of the dual specificity phosphatase family include MAP kinase phosphatase-1 (MKP-1), which dephosphorylates MAP kinase on both threonine and tyrosine residues and a human, vaccinia H1-related phosphatase (VHR), which also removes the phosphate from phosphothreonine and phosphotyrosine residues. Dual specificity phosphatases are exemplified by the VH1 or vaccinia virus late H1 gene protein, which hydrolyzes both phosphotyrosine, phosphothreonine, and phosphoserine. VH1 catalytic activity is required for viral replication. A human homolog of VH1, VHR, has been identified. The three dimensional structure of this family is based on models from x-ray crystallographic data of protein tyrosine phosphatases, and human VHR. The VHR structure includes a core domain consisting of a five-stranded mixed β-sheet and six α-helices. This structure closely superimposes on the structure of phosphotyrosine protein phosphatases. However, dual specificity phosphatases lack the KNRY motif, and the N-terminal structures of tyrosine protein phosphatases which endow these enzymes with a deep active site specific for aryl phosphates. Thus, dual specificity phosphatases have a shallower active site relative to tyrosine protein phosphatases and can accommodate phosphoserine and phosphothreonine substrates. Even so dual specificity phosphatases can have a greater than 50-fold faster rate of phosphatase activity for phosphotyrosine substrates than phosphothreonine or phosphoserine substrates.

Similar to the broader class of phosphatases, dual specificity phosphatases have a highly conserved active site including three catalytic residues, a cysteine, an arginine, and an aspartic acid. The active site cysteine and arginine are found in the "C—$X_5$—R" motif of the tyrosine phosphatase signature (Prosite PS00383). This motif forms a binding pocket for three of the phosphate oxyanions. The cysteine acts as a nucleophile to accept the $PO_3$ group. The reaction transiently generates a phospho-cysteine intermediate before the phosphate is transferred to water. The active site arginine stabilizes the transition-state by hydrogen bonding to phosphate oxygens. In addition the histidine preceding the active site cysteine and the serine or threonine following the active site arginine are responsible for lowering the $pK_a$ of the cysteine to stabilize a negative charge on the cysteine. The active site aspartic acid accelerates the reaction by donating a protein to generate an uncharged hydroxyl (for a review, see Fauman and Saper (1996) *Trends in Biochem.* 21:412). A C—$X_5$—R motif is found at about amino acids 150 to 156 of SEQ ID NO:2.

The 18232 proteins of the present invention show significant homology to members of the dual specificity phosphatase family, and in particular, vaccinia H1-related phosphatases (VHRs). Dual specificity phosphatases are known to play critical roles in growth factor signaling. For example, VHR-like phosphatases are known to dephosphorylate growth factor receptors and thereby eliminate their signaling. MAP-kinase phosphatases terminate MAP-kinase activity, thus leading to inhibition of growth factor-mediated mitogenic signaling. Thus, dual specificity phosphatases play a key role in inhibiting proliferation and stimulating the differentiation of cells. As the 18232 proteins show homology to dual specificity phosphatases, these proteins are likely to be involved in modulating (e.g., inhibiting) the proliferation and (e.g., stimulating) the differentiation of the cells in which they are expressed, e.g., hematopoietic cells such as blood cells, e.g., erythroid cells. Accordingly, the 18232 molecules of the invention may be useful for developing novel diagnostic and therapeutic agents for 18232-mediated or related disorders, as described below.

A 18232 polypeptide of the invention can include a "dual specificity phosphatase catalytic domain" or regions homologous with a "dual specificity phosphatase catalytic domain". As used herein, the term "dual specificity phosphatase catalytic domain" refers to an amino acid sequence having about 50 to 200, preferably about 75 to 175, more preferably about 100 to 150, and even more preferably about 130 to 145 amino acid residues, and having a bit score for the alignment of the sequence to the dual specificity phosphatase domain (HMM) of the Pfam database of at least 50, preferably 100, and more preferably 120, or 140 or more. The dual specificity phosphatase catalytic domain (HMM) has been assigned the PFAM Accession PF00782. An alignment of the dual specificity phosphatase catalytic domain (amino acids 18–156 of SEQ ID NO:2) of human 18232 with a consensus amino acid sequence (SEQ ID NO:4) derived from a hidden Markov model in the Pfam database is depicted in FIGS. 3A, and a similar alignment with a consensus amino acid sequence (SEQ ID NO:5) derived from the SMART database HMM model is depicted in FIG. 3B.

A dual specificity phosphatase domain preferable includes the conserved active site cysteine and arginine in a C—$X_5$—R motif found at about amino acids 103 to 109 of SEQ ID NO:2. Preferably, the dual specificity phosphatase domain includes a conserved general acid, e.g., an aspartic acid which participates in catalysis. For example, a 18232 protein has an aspartic acid located at about residue 74 of SEQ ID NO:2, located in a VH1-like dual specificity phosphatase loop located at about amino acid residues 70 to 74 of SEQ ID NO:2. Typically, dual specificity phosphatases are able to dephosphorylate tyrosine residues and serine/threonine residues.

In a preferred embodiment, a 18232 polypeptide or protein has a "dual specificity phosphatase catalytic domain" or a region that includes at least about 50 to 200, preferably about 75 to 175, more preferably about 100 to 150, and even more preferably about 120 to 140 amino acid residues and has at least about 70%, 80%, 90%, 95%, 99%, or 100% homology with a "dual specificity phosphatase catalytic domain," e.g., the dual specificity phosphatase catalytic domain of human 18232 (e.g., residues 18 to 156 of SEQ ID NO:2).

To identify the presence of a "dual specificity phosphatase catalytic domain" in a 18232 protein sequence and to make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the HMM database resulting in the identification of a "dual specificity phosphatase catalytic domain" in the amino acid sequence of human 18232 at about residues 18–156 of SEQ ID NO:2 (see FIGS. 3A–3B).

A 18232 molecule can further include: at least one, preferably two protein kinase C phosphorylation sites; at least one, two, or preferably three N-myristylation sites; preferably at least one N-glycosylation site; and preferably at least one amidation site.

As used herein, "18232 activity", "biological activity of 18232" or "functional activity of 18232", refers to an activity exerted by a 18232 protein, polypeptide or nucleic acid molecule on e.g., a 18232-responsive cell or on a 18232 substrate, e.g., a protein substrate, as determined in vivo or in vitro. In one embodiment, a 18232 activity is a direct activity, such as an association with a 18232 target molecule. A "target molecule" or "binding partner" is a molecule with which a 18232 protein binds or interacts with in nature, e.g., a protein containing one or more phosphotyrosine, phosphoserine, or phosphothreonine residues. A 18232 activity also can be an indirect activity, e.g., a cellular signaling activity mediated by interaction of the 18232 protein with a 18232 receptor (e.g., a cytokine receptor).

Based on the above-described sequence similarities, the 18232 molecules of the present invention are predicted to have similar biological activities as dual specificity phosphatase family members. Dual specificity phosphatases are known to play critical roles in the regulation of numerous cellular processes, including hematopoiesis. These phosphatases have been shown to associate with activated receptors, e.g., cytokine receptors, and to modulate (e.g., inhibit) growth factor signaling by dephosphorylating receptors, e.g., cytokine receptors, thereby negatively regulating mitogenic signaling. Protein phosphatases have also been shown to regulate transcriptional activity, e.g., cytokine transcriptional activity, stimulated by protein kinases such as JAK/STAT and MAP kinase pathways. Therefore, protein phosphatases are likely to be involved in regulating the signaling machinery responsible for cell differentiation of, e.g., hematopoietic (e.g., blood) cells, and/or modulation, e.g., suppression, of apoptosis.

Based on the sequence similarity and tissue distribution described below, the 18232 molecules of the invention are predicted to have one or more of the following activities: (1) catalyze the removal of a phosphate group attached to a tyrosine residue in a protein target, e.g., a growth factor (e.g., cytokine) receptor; (2) catalyze the removal of a phosphate group attached to a serine or threonine residue in a protein e.g., a growth factor (e.g., cytokine) receptor; (3) modulate growth factor (e.g., cytokine) activity; (4) modulate an intracellular signaling pathway, e.g., a MAP kinase, JAK/STAT, ERK kinase pathway; (5) modulate (e.g., stimulate) cell differentiation, e.g., differentiation of hematopoietic cells (e.g., differentiation of blood cells (e.g., erythroid progenitor cells, such as CD34+ erythroid progenitors)); (6) modulate hematopoiesis, e.g., erythropoiesis; (7) modulate cell proliferation, e.g., proliferation of hematopoietic cells (e.g., erythroid progenitor cells); (8) inactivate cell surface growth factor receptors, e.g., cytokine receptors; (9) modulate apoptosis, of a cell, e.g., increase apoptosis of a cancer cell, e.g., a leukemic cell, (e.g., an erythroleukemia cell); or suppress apoptosis of a blood or erythroid cell; or (10) modulate transcriptional activity, e.g., cytokine transcriptional activity.

The molecules of the invention can be used to develop novel agents or compounds to treat and/or diagnose disorders involving aberrant activities of the cells in which 18232 nucleic acids and polypeptides are expressed. 18232 mRNA is found primarily in hematopoietic progenitor CD34 cells (FIGS. 4–7). Its expression is further enhanced in the erythroid lineage and increases as bone marrow/blood cell differentiation proceeds. This pattern of expression suggests a role for 18232 in the regulation of cytokine signaling during the development of cells of the erythroid lineage.

More specifically, significant expression of 18232 mRNA is found in the bone marrow, cord blood, fetal liver, and in particular, in CD34– expressing populations of cells from those tissues, such as mobilized peripheral blood CD34+ cells, normal adult bone marrow CD34+ cells, cord blood CD34+ cells, normal adult bone marrow CD34+ cells, and fetal liver CD34+ cells; as well as erythroid progenitor cells, e.g., bone marrow glycophorin A positive cells, erythropoietin treated erythroid burst forming units (BFUs), erythrocytes, in vitro generated erythroblasts, and megakaryocytes (FIGS. 4–7). 18232 mRNA is also expressed in epithelial cells, kidney, skeletal muscle, fetal and adult heart, spinal cord, brain, lung, and cell lines K562, HepG2, Hep3B, HL60 and Molt4. Thus, diagnostic and therapeutic methods using the molecules of the invention (or agents that modulate the activity or expression of the 18232 molecules) to treat/diagnose disorders involving the cells/tissues expressing 18232 molecules are contemplated by the present invention.

As used herein, a "CD34-positive cell" or a "CD34-expressing cell" refers to a cell that expresses detectable levels of the CD34 antigen, preferably human CD34 antigen. The sequence for human CD34 is provided in SwissProt Accession Number P28906. The CD34 antigen is typically present on immature hematopoietic precursor cells and hematopoietic colony-forming cells in the bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)-positive B- and T-lymphoid precursors in normal bone also are CD34+. The CD34 antigen is typically present on early myeloid cells that express the CD33 antigen, but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early hematopoietic progenitor cells and decreases as the cells mature. The antigen is undetectably on fully differentiated hematopoietic cells. Approximately 60% of acute B-lymphoid leukemia's and acute myeloid leukemia express the CD34 antigen. The antigen is not expressed on chronic lymphoid leukemia (B or T lineage) or lymphomas.

As the 18232 polypeptides of the invention may modulate 18232-mediated activities, they may be useful as of for developing novel diagnostic and therapeutic agents for 18232-mediated or related disorders, e.g., blood cell-(e.g., erythroid-) associated disorders and other hematopoietic disorders.

As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, drug-(chemotherapy-) induced anemias, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in non-hematolic disorders, for example, as a result of chemotherapy, alcoholism, or liver disease; anemia of chronic disease, such as chronic renal failure; and endocrine deficiency diseases.

Agents that modulate 18232 polypeptide or nucleic acid activity or expression can be used to treat anemias, in particular, drug-induced anemias or anemias associated with cancer chemotherapy, chronic renal failure, malignancies, adult and juvenile rheumatoid arthritis, disorders of hemoglobin synthesis, prematurity, and zidovudine treatment of HIV infection. A subject receiving the treatment can be additionally treated with a second agent, e.g., erythropoietin, to further ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, *Ann. Rev. Med.* 29:51 (1978); Eschbach and Adamson, *Kidney Intl.* 28:1 (1985). Recombinant human erythropoietin (rHuEpo or epoietin alpha) is commercially available as EPOGEN.RTM. (epoietin alpha, recombinant human erythropoietin) (Amgen Inc., Thousand Oaks, Calif.) and as PROCRIT.RTM. (epoietin alpha, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

Aberrant expression or activity of the 18232 molecules may be involved in neoplastic disorders. Accordingly, treatment, prevention and diagnosis of cancer or neoplastic disorders related to hematopoietic cells and, in particular, cells of the erythroid lineage are also included in the present invention. Such neoplastic disorders are exemplified by erythroid leukemias, or leukemias of erythroid precursor cells, e.g., poorly differentiated acute leukemias such as erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol/Hemotol.* 11:267–97). In particular, AML can include the uncontrolled proliferation of CD34+ cells such as AML subtypes M1 and M2, myeloblastic leukemias with and without maturation, and AML subtype M6, erythroleukemia (Di Guglielmo's disease). Additional neoplastic disorders include a myelodysplastic syndrome or preleukemic disorder, e.g., oligoblastic leukemia, smoldering leukemia. Additional cancers of the erythroid lineage include erythroblastosis, and other relevant diseases of the bone marrow.

The term "leukemia" or "leukemic cancer" is intended to have its clinical meaning, namely, a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

The molecules of the invention may also modulate the activity of neoplastic, non-hematopoietic tissues in which they are expressed, e.g., kidney, lung, liver, skeletal muscle. For example, increase expression of 18232 molecules is detected on lung tumors compared to the normal lung. Accordingly, the 18232 molecules can act as novel diagnostic targets and therapeutic agents for controlling one or more of cellular proliferative and/or differentiative disorders. Examples of such cellular proliferative and/or differentiative disorders include cancer, e.g., carcinoma, sarcoma, or metastatic disorders. A metastatic tumor can arise from a multitude of primary tumor types, including but not limited to those of lung, prostate, colon, breast, and liver origin.

As used herein, the terms "cancer", "hyperproliferative", and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as those affecting lung, breast, thyroid, lymphoid, gastrointestinal, and the genitourinary tract. The terms "cancer" or "neoplasms" also includes adenocarcinomas that include malignancies such as most colon cancers, renal-cell carcinoma, prostate cancer and/or testicular tumors, non-small cell carcinoma of the lung, cancer of the small intestine, and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon, and ovary. The term also includes carcinosarcomas, e.g., malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 18232 protein, fragments thereof, and derivatives and other variants of the sequence in SEQ ID NO:2 thereof are collectively referred to as "polypeptides or proteins of the invention" or "18232 polypeptides or proteins". Nucleic acid molecules encoding such polypeptides or proteins are collectively referred to as "nucleic acids of the invention" or "18232 nucleic acids." 18232 molecules refer to 18232 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with respect to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4kb, 3kb, 2kb, I kb, 0.5 kb or 0.1 kb of 5' and/or 3' nucleotide sequences that naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in Current Protocols in Molecular Biology, John Wiley & Sons, N.Y. (1989), 6.3.1–6.3.6. Aqueous and nonaqueous methods are described in that reference and either can be used. A preferred example of stringent hybridization conditions includes hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a sequence is within the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NOs:1 or 3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules that include an open reading frame encoding a 18232 protein, preferably a mammalian 18232 protein, and further can include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 18232 protein having less than about 30%, 20%, 10% and more preferably 5% (by dry weight), of non-18232 protein (also referred to herein as a "contaminating protein"), or of chemical precursors or non-18232 chemicals. When the 18232 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 18232 (e.g., the sequence of SEQ ID NO:1 or 3) without abolishing or more preferably, without substantially altering a biological activity of the 18232 protein, whereas an "essential" amino acid residue results in such a change. For example, amino acid residues that are conserved among the polypeptides of the present invention, e.g., those present in the dual specificity phosphatase catalytic domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 18232 protein is preferably replaced with another amino acid residue from the same side chain family. Alternatively, in another embodiment, mutations can be introduced randomly along all or part of a 18232 coding sequence, such as by saturation mutagenesis, and the resultant mutants can be screened for 18232 biological activity to identify mutants that retain activity. Following mutagenesis of SEQ ID NO:1 or 3 the encoded protein can be expressed recombinantly and the activity of the protein can be determined.

As used herein, a "biologically active portion" of a 18232 protein includes a fragment of a 18232 protein that participates in an interaction between a 18232 molecule and a non-18232 molecule. Biologically active portions of a 18232 protein include peptides comprising amino acid sequences sufficiently homologous to or derived from the amino acid sequence of the 18232 protein, e.g., the amino acid sequence shown in SEQ ID NO:2, which include less amino acids than the full length 18232 protein and exhibit at least one activity of a 18232 protein. Typically, biologically active portions comprise a domain or motif with at least one activity of the 18232 protein, e.g., dual specificity phosphatase activity. A biologically active portion of a 18232 protein can be a polypeptide that is, for example, 10, 25, 50, 100, 150 or more amino acids in length. Biologically active portions of a 18232 protein can be used as targets for developing agents that modulate a 18232 mediated activity, e.g., dual specificity phosphatase activity.

Particular 18232 polypeptides of the present invention have an amino acid sequence sufficiently identical to the amino acid sequence of SEQ ID NO:2. The term "sufficiently identical" or "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%. 91%, 92%, 93%, 94%, 95%, 96%, 97%, 98% or 99% identity are defined herein as sufficiently or substantially identical.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 18232 amino acid sequence of SEQ ID NO:2 having 59 amino acid residues, at least 70, preferably at least 88, more preferably at least 106, even more preferably at least 123, and even more preferably at least 141, 158, or 176 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

"Misexpression or aberrant expression", as used herein, refers to a non-wild type pattern of gene expression at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental animal or disease model. The subject also can be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides an isolated or purified nucleic acid molecule that encodes a 18232 polypeptide described herein, e.g., a full length 18232 protein or a fragment thereof, e.g., a biologically active portion of a 18232 protein. Also included is a nucleic acid fragment suitable for use as a hybridization probe, which can be used, e.g., to identify a nucleic acid molecule encoding a polypeptide of the invention, 18232 mRNA, or fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of this nucleotide sequence. In one embodiment, the nucleic acid molecule includes sequences encoding the 18232 protein (i.e., "the coding region", from nucleotides 329–859 of SEQ ID NO:1), as well as 5' untranslated sequences (nucleotides 1–328 of SEQ ID NO:1). Alternatively, the nucleic acid molecule can include only the coding region of SEQ ID NO:1 (e.g., nucleotides 329–859, corresponding to SEQ ID NO:3) and, e.g., no flanking sequences that normally accompany the subject sequence. In another embodiment, the nucleic acid molecule encodes a sequence corresponding to the mature protein from about amino acid 1 to amino acid 176 of SEQ ID NO:2.

In another embodiment, an isolated nucleic acid molecule of the invention includes a nucleic acid molecule that is a complement of the nucleotide sequence shown in SEQ ID NO:1 or 3, or a portion of either of these nucleotide sequences. In other embodiments, the nucleic acid molecule of the invention is sufficiently complementary to the nucleotide sequence shown in SEQ ID NO:1 or 3 such that it can hybridize to the nucleotide sequence shown in SEQ ID NO:1 or 3 thereby forming a stable duplex.

In one embodiment, an isolated nucleic acid molecule of the present invention includes a nucleotide sequence that is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or 3. In the case of an isolated nucleic acid molecule which is longer than or equivalent in length to the reference sequence, e.g., SEQ ID NO:1, the comparison is made with the full length of the reference sequence. Where the isolated nucleic acid molecule is shorter that the reference sequence, e.g., shorter than SEQ ID NO:1, the comparison is made to a segment of the reference sequence of the same length (excluding any loop required by the homology calculation).

18232 Nucleic Acid Fragments

A nucleic acid molecule of the invention can include only a portion of the nucleic acid sequence of SEQ ID NO:1 or 3. For example, such a nucleic acid molecule can include a fragment that can be used as a probe or primer or a fragment encoding a portion of a 18232 protein, e.g., an immunogenic or biologically active portion of a 18232 protein. A fragment can comprise nucleotides 380 to 796 of SEQ ID NO:1, which encodes a dual specificity phosphatase catalytic domain of human 18232. The nucleotide sequence determined from the cloning of the 18232 gene allows for the generation of probes and primers designed for use in identifying and/or cloning other 18232 family members, or fragments thereof, as well as 18232 homologues or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid fragment described herein. Nucleic acid fragments can encode a specific domain or site described herein or fragments thereof, particularly fragments thereof which are at least 400 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment also can include one or more domains, regions, or functional sites described herein. Thus, for example, the nucleic acid fragment can include a dual specificity phosphatase catalytic domain and an amidation site.

18232 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or 3 of a naturally occurring allelic variant or mutant of SEQ ID NO:1 or 3.

In a preferred embodiment the nucleic acid is a probe that is at least 5 or 10 and less than 500, 300, or 200 base pains in length, and more preferably is less than 100 or less than 50 base pairs in length. It should be identical, or differ by 1, or less than 5 or 10 bases, from a sequence disclosed herein. If alignment is needed for this comparison, the sequences should be aligned for maximum homology. "Looped" out sequences in the alignment from deletions, insertions, or mismatches, are considered differences.

A probe or primer can be derived from the sense or anti-sense strand of a nucleic acid that encodes a dual specificity phosphatase catalytic domain: amino acid residues 18 to 156 of SEQ ID NO:2.

In another embodiment a set of primers is provided, e.g., primers suitable for use in a PCR, which can be used to amplify a selected region of a 18232 sequence, e.g., one of the ones described herein. The primers should be at least 5, 10, or 50 base pairs in length and less than 100 or 200 base pairs in length. The primers should be identical, or differ by one base from a sequence disclosed herein or from a naturally occurring variant. E.g., primers suitable for amplifying all or a portion of the dual specificity phosphatase catalytic domain (amino acid residues 18 to 156 of SEQ ID NO:2).

A nucleic acid fragment can encode an epitope bearing region of a polypeptide described herein.

A nucleic acid fragment encoding a "biologically active portion of a 18232 polypeptide" can be prepared by isolating a portion of the nucleotide sequence of SEQ ID NO:1 or 3 which encodes a polypeptide having a 18232 biological activity (e.g., the biological activities of the 18232 proteins described herein), expressing the encoded portion of the 18232 protein (e.g., by recombinant expression in vitro) and assessing the activity of the encoded portion of the 18232 protein. For example, a nucleic acid fragment encoding a biologically active portion of 18232 includes a dual specificity phosphatase catalytic domain, e.g., amino acid residues 18 to 156 of SEQ ID NO:2. A nucleic acid fragment encoding a biologically active portion of a 18232 polypeptide, may comprise a nucleotide sequence that is greater than about 300 or more nucleotides in length (e.g., greater than about 400 nucleotides in length).

In a preferred embodiment, the fragment is at least 381, 400, 450, 500, 550, 600, 650, 700, 750, 800, 850, 900, 950, or 1000 nucleotides in length, or more nucleotides in length and hybridizes under stringent hybridization conditions to a nucleic acid molecule of SEQ ID NO:1 or SEQ ID NO:3.

In a preferred embodiment, a nucleic acid fragment includes a nucleotide sequence comprising nucleotides SEQ ID NO:1 or SEQ ID NO:3, or a portion thereof, wherein each portion is about 381 or longer nucleotides and hybridizes under stringent hybridization conditions to a nucleic acid molecule of SEQ ID NO:1 or SEQ ID NO:3.

In a preferred embodiment, a nucleic acid fragment has a nucleotide sequence other than (e.g., differs by at least one, two, three, five, ten or more nucleotides from) the nucleotide sequence of sequence of AI 018626, AW 206269, AI 672432, AI 034374, AA 700744, AI 027213, AI 498377, AI 950221, AI 016945, or AI 040185.

18232 Nucleic Acid Variants

The invention further encompasses nucleic acid molecules that differ from the nucleotide sequence shown in SEQ ID NO:1 or 3. Such differences can be due to degeneracy of the genetic code (and result in a nucleic acid that encodes the same 18232 proteins as those encoded by the nucleotide sequence disclosed herein. In another embodiment, an isolated nucleic acid molecule of the invention has a nucleotide sequence encoding a protein having an amino acid sequence that differs by at least 1, but less than 5, 10, 20, 50, or 100 amino acid residues than that shown in SEQ ID NO:2. If alignment is needed for this comparison the sequences should be aligned for maximum homology. "Looped" out sequences from deletions, insertions, or mismatches, are considered differences.

Nucleic acids of the invention can be chosen for having codons, which are preferred, or non-preferred, for a particular expression system. E.g., the nucleic acid can be one in which at least one codon, at preferably at least 10%, or 20% of the codons has been altered such that the sequence is optimized for expression in *E. coli,* yeast, human, insect, or Chinese hamster ovary (CHO) cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared with the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. If necessary for this analysis, the sequences should be aligned for maximum homology. "Looped" out sequences from deletions, insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or a fragment of this sequence. Such nucleic acid molecules can readily be identified as being able to hybridize under stringent conditions, to the nucleotide sequence shown in SEQ ID NO 1 or a fragment of the sequence. Nucleic acid molecules corresponding to orthologs, homologs, and allelic variants of the 18232 cDNAs of the invention can further be isolated by mapping to the same chromosome or locus as the 18232 gene. Preferred variants include those that are correlated with tyrosine phosphatase activity.

Allelic variants of 18232, e.g., human 18232, include both functional and non-functional proteins. Functional allelic variants are naturally occurring amino acid sequence variants of the 18232 protein within a population that maintain the ability to remove the phosphate from a tyrosine, serine, or threonine residue of a phosphorylated protein. Functional allelic variants typically will contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 18232, e.g., human 18232, protein within a population that do not have the ability to remove the phosphate from a tyrosine serine, or threonine residue of a phosphorylated protein. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 18232 family members and, thus have a nucleotide sequence that differs from the 18232 sequences of SEQ ID NO:1 or 3 are intended to be within the scope of the invention.

Antisense Nucleic Acid Molecules, Ribozymes and Modified 18232 Nucleic Acid Molecules In another aspect, the invention features, an isolated nucleic acid molecule that is antisense to 18232. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 18232 coding strand, or to only a portion thereof (e.g., the coding region of 18232 corresponding to SEQ ID NO:3). In another embodiment, the antisense nucleic acid molecule is antisense to a "noncoding region" of the coding strand of a nucleotide sequence encoding 18232 (e.g., the 5' and 3' untranslated regions).

An antisense nucleic acid can be designed such that it is complementary to the entire coding region of 18232 mRNA, but more preferably is an oligonucleotide that is antisense to only a portion of the coding or noncoding region of 18232 mRNA. For example, the antisense oligonucleotide can be complementary to the region surrounding the translation start site of 18232 mRNA, e.g., between the −10 and +10 regions of the target gene nucleotide sequence. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions with procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 18232 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong polymerase II or polymerase III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 18232-encoding nucleic acid can include one or more sequences complementary to the nucleotide sequence of a 18232 cDNA disclosed herein (i.e., SEQ ID NO:1 or 3), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 18232-encoding mRNA. See, e.g., Cech et al. U.S. Pat. No. 4,987,071; and Cech et al. U.S. Pat. No. 5,116,742. Alternatively, 18232 mRNA can be used to select a catalytic RNA having a specific ribonuclease activity from a pool of RNA molecules. See, e.g., Bartel, D. and Szostak, J. W. (1993) *Science* 261:1411–1418.

18232 gene expression can be inhibited by targeting nucleotide sequences complementary to the regulatory region of the 18232 (e.g., the 18232 promoter and/or enhancers) to form triple helical structures that prevent transcription of the 18232 gene in target cells. See generally, Helene, C. (1 991) *Anticancer Drug Des.* 6(6):569–84; Helene, C. et al. (1992) *Ann. N.Y Acad. Sci.* 660:27–36; and Maher, L. J. (1992) *Bioassays* 14(12):807–15. The potential sequences that can be targeted for triple helix formation can be increased by creating a "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 18232 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acid" or "PNA" refers to a nucleic acid mimic, e.g., a DNA mimic in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of 18232 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 18232 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region that is complementary to a 18232 nucleic acid of the invention. The molecular beacon primer and probe molecules also have two complementary regions, one having a fluorophore and one having a quencher, such that the molecular beacon is useful for quantitating the presence of a 18232 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. 5,876,930.

Isolated 18232 Polypeptides

In another aspect, the invention features an isolated 18232 protein or fragment thereof, e.g., a biologically active portion for use as immunogens or antigens to raise or test (or more generally to bind) anti-18232 antibodies. 18232 protein can be isolated from cells or tissue sources using standard protein purification techniques. 18232 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and posttranslational events. The polypeptide can be expressed in systems, e.g., cultured cells, which result in substantially the same posttranslational modifications present when expressed the polypeptide is expressed in a native cell, or in systems which result in the alteration or omission of posttranslational modifications, e.g., glycosylation or cleavage, present when expressed in a native cell.

In a preferred embodiment, a 18232 polypeptide has one or more of the following characteristics:

(i) it has the ability to promote removal of phosphate from phosphorylated tyrosine, serine, or threonine residues of protein;

(ii) it has a molecular weight (e.g., a deduced molecular weight), amino acid composition or other physical characteristic of a 18232 protein of SEQ ID NO:2;

(iii) it has an overall sequence similarity of at least 60%, more preferably at least 70, 80, 90, or 95%, with a polypeptide encoded by SEQ ID NO:2;

(iv) it has a phosphatase catalytic domain which is preferably about 70%, 80%, 90% or 95% with amino acid residues 18–156 of SEQ ID NO:2; or (v) it has at least 70%, preferably at least 80%, and most preferably at least 95% of the cysteines found in the amino acid sequence of the native protein.

In a preferred embodiment, the 18232 protein or fragment thereof differs from the corresponding sequence in SEQ ID NO:2. In one embodiment, it differs by at least one but by less than 15, 10 or 5 amino acid residues. In another embodiment, it differs from the corresponding sequence in SEQ ID NO:2 by at least one residue but less than 20%, 15%, 10% or 5% of the residues in it differ from the corresponding sequence in SEQ ID NO:2. (If this comparison requires alignment, the sequences should be aligned for maximum homology. "Looped" out sequences from deletions, insertions, or mismatches, are considered differences.) The differences are, preferably, differences or changes at a non-essential residue or a conservative substitution. In a preferred embodiment, the differences are not in the dual specificity phosphatase catalytic domain. In another preferred embodiment one or more differences are at non-active site residues, e.g., amino acids 1–17, or 157–176 of SEQ ID NO:2.

Other embodiments include a protein that contains one or more changes in amino acid sequence, e.g., a change in an amino acid residue that is not essential for activity. Such 18232 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2.

A 18232 protein or fragment is provided which varies from the sequence of SEQ ID NO:2 in non-active site residues by at least one but by less than 15, 10 or 5 amino acid residues in the protein or fragment, but which does not differ from SEQ ID NO:2 in regions having phosphatase catalytic activity. (If this comparison requires alignment the sequences should be aligned for maximum homology. "Looped" out sequences from deletions, insertions, or mismatches, are considered differences.) In some embodiments, the difference is at a non essential residue or is a conservative substitution, while in others, the difference is at an essential residue or is a non conservative substitution.

In one embodiment, a biologically active portion of a 18232 protein includes a dual specificity phosphatase catalytic domain. Moreover, other biologically active portions, in which other regions of the protein are deleted, can be prepared by recombinant techniques and evaluated for one or more of the functional activities of a native 18232 protein.

In a preferred embodiment, the 18232 protein has an amino acid sequence shown in SEQ ID NO:2. In other embodiments, the 18232 protein is substantially identical to SEQ ID NO:2. In yet another embodiment, the 18232 protein is substantially identical to SEQ ID NO:2 and retains the functional activity of the protein of SEQ ID NO:2, as described in detail in the subsections above. Accordingly, in another embodiment, the 18232 protein is a protein which includes an amino acid sequence at least about 60%, 65%, 70%, 75%, 80%, 85%, 90%, 95%, 98% or more identical to SEQ ID NO:2.

18232 Chimeric or Fusion Proteins

In another aspect, the invention provides 18232 chimeric or fusion proteins. As used herein, a 18232 "chimeric protein" or "fusion protein" includes a 18232 polypeptide linked to a non-18232 polypeptide. A "non-18232 polypeptide" refers to a polypeptide having an amino acid sequence corresponding to a protein that is not substantially homologous to the 18232 protein, e.g., a protein that is different from the 18232 protein and that is derived from the same or a different organism. The 18232 polypeptide of the fusion protein can correspond to all or a portion e.g., a fragment described herein of a 18232 amino acid sequence. In a preferred embodiment, a 18232 fusion protein includes at least one (e.g. two) biologically active portion of a 18232 protein. The non-18232 polypeptide can be fused to the N-terminus or C-terminus of the 18232 polypeptide.

The fusion protein can include a moiety that has high affinity for a ligand. For example, the fusion protein can be a GST-18232 fusion protein in which the 18232 sequences are fused to the C-terminus of the GST sequences. Such fusion proteins can facilitate the purification of recombinant 18232. Alternatively, the fusion protein can be a 18232 protein containing a heterologous signal sequence at its N-terminus. In certain host cells (e.g., mammalian host cells), expression and/or secretion of 18232 can be increased through use of a heterologous signal sequence.

Fusion proteins can include all or a part of a serum protein, e.g., an IgG constant region, or human serum albumin.

The 18232 fusion proteins of the invention can be incorporated into pharmaceutical compositions and administered to a subject in vivo. The 18232 fusion proteins can be used to affect the bioavailability of a 18232 substrate. 18232 fusion proteins may be useful therapeutically for the treatment of disorders caused by, for example, (i) aberrant modification or mutation of a gene encoding a 18232 protein; (ii) mis-regulation of the 18232 gene; and (iii) aberrant post-translational modification of a 18232 protein.

Moreover, 18232-fusion proteins of the invention can be used as immunogens to produce anti-18232 antibodies in a subject, to purify 18232 ligands, and in screening assays to identify molecules that inhibit the interaction of 18232 with a 18232 substrate.

Expression vectors are commercially available that already encode a fusion moiety (e.g., a GST polypeptide). A 18232-encoding nucleic acid can be cloned into such an expression vector such that the fusion moiety is linked in-frame to the 18232 protein.

Variants of 18232 Proteins

In another aspect, the invention features a variant of a 18232 polypeptide, e.g., a polypeptide that functions as an agonist (mimetic) or as an antagonist of 18232 activities. Variants of the 18232 proteins can be generated by mutagenesis, e.g., discrete point mutations, the insertion or deletion of sequences or the truncation of a 18232 protein. An agonist of the 18232 protein retains substantially the same, or a subset, of the biological activities of the naturally occurring form of a 18232 protein. An antagonist of a 18232 protein can inhibit one or more of the activities of the naturally occurring form of the 18232 protein by, for example, competitively modulating a 18232-mediated activity of a 18232 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 18232 protein.

Variants of a 18232 protein can be identified by screening combinatorial libraries of mutants, e.g., truncation mutants, of a 18232 protein for agonist or antagonist activity.

Libraries of fragments e.g., N terminal, C terminal, or internal fragments, of a 18232 protein coding sequence can be used to generate a variegated population of fragments for screening and subsequent selection of variants of a 18232 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property are known. Recursive ensemble mutagenesis (REM), a new technique which enhances the frequency of functional mutants in the libraries, can be used in combination with screening assays to identify 18232 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 18232 library. For example, a library of expression vectors can be transfected into a cell line, e.g., a cell line, which ordinarily responds to 18232 in a substrate-dependent manner. The transfected cells are then contacted with 18232 and the effect of the expression of the mutant on signaling by the 18232 substrate can be detected, e.g., by measuring loss of phosphorylation of tyrosine, serine, or threonine residues. Plasmid DNA can then be recovered from the cells that score for inhibition, or alternatively, potentiation of signaling by the 18232 substrate, and the individual clones further characterized.

In another aspect, the invention features a method of making a 18232 polypeptide, e.g., a peptide having a non-wild type activity, e.g., an antagonist, agonist, or super agonist of a naturally occurring 18232 polypeptide, e.g., a naturally occurring 18232 polypeptide. The method includes: altering the sequence of a 18232 polypeptide, e.g., by substitution or deletion of one or more residues of a non-conserved region, a domain or residue disclosed herein, and testing the altered polypeptide for the desired activity.

In another aspect, the invention features a method of making a fragment or analog of a 18232 polypeptide that retains at least one biological activity of a naturally occurring 18232 polypeptide. The method includes: altering the sequence, e.g., by substitution or deletion of one or more residues, of a 18232 polypeptide, e.g., altering the sequence of a non-conserved region, or a domain or residue described herein, and testing the altered polypeptide for the desired activity.

Anti-18232 Antibodies

In another aspect, the invention provides an anti-18232 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments that can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 18232 protein, or antigenic peptide fragment of 18232, can be used as an immunogen or can be used to identify anti-18232 antibodies made with other immunogens, e.g., cells, membrane preparations, and the like. The antigenic peptide of 18232 should include at least 8 amino acid residues of the amino acid sequence shown in SEQ ID NO:2 and encompasses an epitope of 18232. Preferably, the antigenic peptide includes at least 10 amino acid residues, more preferably at least 15 amino acid residues, even more preferably at least 20 amino acid residues, and most preferably at least 30 amino acid residues.

Fragments of 18232 that include residues 51–61, 101–111, or 131–155 of SEQ ID NO:2 can be used to make, e.g., used as immunogens or used to characterize the specificity of an antibody, antibodies against regions of the 18232 protein which are believed to be hydrophilic. Similarly, a fragment of 18232 that includes residues 11–31, 38–51, or 81–101 of SEQ ID NO:2 can be used to make an antibody against regions of the 18232 protein which are believed to be hydrophobic; a fragment of 18232 that includes residues 18–28, 38–68, or 128–156 of SEQ ID NO:2 can be used to make an antibody against the dual specificity phosphatase catalytic region of the 18232 protein.

Antibodies reactive with, or specific for, any of these regions, or other regions or domains described herein are provided.

Preferred epitopes encompassed by the antigenic peptide are regions of 18232 that are located on the surface of the protein, e.g., hydrophilic regions, as well as regions with high antigenicity. For example, an Emini surface probability analysis of the human 18232 protein sequence can be used to indicate the regions that have a particularly high probability of being localized to the surface of the 18232 protein and are thus likely to constitute surface residues useful for targeting antibody production.

In a preferred embodiment the antibody binds an epitope on any domain or region on 18232 proteins described herein.

Chimeric, humanized, but most preferably, completely human antibodies are desirable for applications which include repeated administration, e.g., therapeutic treatment (and some diagnostic applications) of human patients.

The anti-1 8232 antibody can be a single chain antibody. A single-chain antibody (scFV) may be engineered (see, for example, Colcher, D., et al. (1999) *Ann N Y Acad Sci* Jun 30;880:263–80; and Reiter, Y. (1996) *Clin Cancer Res,* Feb;2(2):245–52). The single chain antibody can be dimerized or multimerized to generate multivalent antibodies having specificities for different epitopes of the same target 18232 protein.

An anti-18232 antibody (e.g., monoclonal antibody) can be used to isolate 18232 by standard techniques, such as affinity chromatography or immunoprecipitation. Moreover, an anti-18232 antibody can be used to detect 18232 protein (e.g., in a cellular lysate or cell supernatant) in order to evaluate the abundance and pattern of expression of the protein. Anti-18232 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin ibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 18232 nucleic acid in a form suitable for expression of the nucleic acid in a host cell.

Preferably, the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 18232 proteins, mutant forms of 18232 proteins, fusion proteins, and the like).

The recombinant expression vectors of the invention can be designed for expression of 18232 proteins in prokaryotic or eukaryotic cells. For example, polypeptides of the invention can be expressed in *E. coli,* insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.), which fuse glutathione S-transferase (GST), maltose E binding protein, and protein A, respectively, to the target recombinant protein.

Purified fusion proteins can be used in 18232 activity assays, (e.g., direct assays or competitive assays described in detail below), or to generate antibodies specific for 18232 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992)

*Nucleic Acids Res.* 20:2111–2118). Such alteration of nucleic acid sequences of the invention can be carried out by standard DNA synthesis techniques.

The 18232 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) Cell 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, including for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The anti sense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics, Vol.* 1(1) 1986.

Another aspect the invention provides a host cell that includes a nucleic acid molecule described herein, e.g., a 18232 nucleic acid molecule within a recombinant expression vector or a 18232 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 18232 protein can be expressed in bacterial cells such as *E. coli,* insect cells, yeast or mammalian cells (such as CHO or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 18232 protein. Accordingly, the invention further provides methods for producing a 18232 protein using the host cells of the invention. In one embodiment, the method includes culturing the host cell of the invention (into which a recombinant expression vector encoding a 18232 protein has been introduced) in a suitable medium such that a 18232 protein is produced. In another embodiment, the method further includes isolating a 18232 protein from the medium or the host cell.

In another aspect, the invention features a cell or purified preparation of cells that include a 18232 transgene, or which otherwise misexpress 18232. The cell preparation can consist of human or non-human cells, e.g., rodent cells such as mouse or rat cells, rabbit cells, or pig cells. In preferred embodiments, the cell or cells include a 18232 transgene, e.g., a heterologous form of a 18232 nucleic acid, e.g., a gene derived from humans (in the case of a non-human cell). The 18232 transgene can be misexpressed, e.g., overexpressed or underexpressed. In other preferred embodiments, the cell or cells include a gene that misexpresses an endogenous 18232 nucleic acid, e.g., disruption in the expression of a gene, e.g., a knockout. Such cells can serve as a model for studying disorders that are related to mutated or misexpressed 18232 alleles or for use in drug screening.

In another aspect, the invention features, a human cell, e.g., a hematopoietic stem cell, transformed with nucleic acid that encodes a 18232 polypeptide.

Also provided are cells (e.g., human cells, e.g., a hematopoietic cell or a fibroblast cell), or a purified preparation thereof, in which an endogenous 18232 is under the control of a regulatory sequence that does not normally control the expression of the endogenous 18232 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 18232 gene. For example, an endogenous 18232 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 18232 protein and for identifying and/or evaluating modulators of 18232 activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 18232 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 18232 protein to particular cells. A transgenic founder animal can be identified based upon the presence of a 18232 transgene in its genome and/or expression of 18232 mRNA in tissues or cells of the animals. A transgenic founder animal can then be used to breed additional animals carrying the transgene. Moreover, transgenic animals carrying a transgene encoding a 18232 protein can further be bred to other transgenic animals carrying other transgenes.

18232 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 18232 protein (e.g., via a recombinant expression vector in a host cell in gene therapy applications), to detect a 18232 mRNA (e.g., in a biological sample) or a genetic alteration in a 18232 gene, and to modulate 18232 activity, as described further below. The 18232 proteins can be used to treat disorders characterized by insufficient or excessive production of a 18232 substrate or production of 18232 inhibitors. In addition, the 18232 proteins can be used to screen for naturally occurring 18232 substrates, to screen for drugs or compounds that modulate 18232 activity, as well as to treat disorders characterized by insufficient or excessive production of 18232 protein or production of 18232 protein forms which have decreased, aberrant or unwanted activity compared to 18232 wild type protein (e.g., imbalance of protein tyrosine kinase and protein tyrosine phosphorylase activities, leading to aberrant proliferation and/or differentiation of hematopoietic cells). Moreover, the anti-18232 antibodies of the invention can be used to detect and isolate 18232 proteins, regulate the bioavailability of 18232 proteins, and modulate 18232 activity.

A method of evaluating a compound for the ability to interact with, e.g., bind, a subject 18232 polypeptide is provided. The method includes: contacting the compound with the subject 18232 polypeptide; and evaluating ability of the compound to interact with, e.g., to bind or form a complex with the subject 18232 polypeptide. This method can be performed in vitro, e.g., in a cell free system, or in vivo, e.g., in a two-hybrid interaction trap assay. This method can be used to identify naturally occurring molecules that interact with a subject 18232 polypeptide. It can also be used to find natural or synthetic inhibitors of a subject 18232 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) that bind to 18232 proteins, have a stimulatory or inhibitory effect on, for example, 18232 expression or 18232 activity, or have a stimulatory or inhibitory effect on, for example, the expression or activity of a 18232 substrate. Compounds thus identified can be used to modulate the activity of target gene products (e.g., 18232 genes) in a therapeutic protocol, to elaborate the biological function of the target gene product, or to identify compounds that disrupt normal target gene interactions.

In one embodiment, the invention provides assays for screening candidate or test compounds that are substrates of a 18232 protein or polypeptide or a biologically active portion thereof. In another embodiment, the invention provides assays for screening candidate or test compounds that bind to or modulate the activity of a 18232 protein or polypeptide or a biologically active portion thereof.

In any screening assay, a 18232 polypeptide which may have, e.g., a dual specificity domain, can be used.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria or spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell that expresses a 18232 protein or biologically active portion thereof is contacted with a test compound, and the ability of the test compound to modulate 18232 activity is determined. Determining the ability of the test compound to modulate 18232 activity can be accomplished by monitoring, for example, phosphatase activity. The cell, for example, can be of mammalian origin, e.g., human.

The ability of the test compound to modulate 18232 binding to a compound, e.g., a 18232 substrate, or to bind to 18232 can also be evaluated. This can be accomplished, for example, by coupling the compound, e.g., the substrate with a radioisotope or enzymatic label such that binding of the compound, e.g., the substrate, to 18232 can be determined by detecting the labeled compound, e.g., substrate, in a complex. Alternatively, 18232 can be coupled with a radioisotope or enzymatic label to monitor the ability of a test compound to modulate 18232 binding to a 18232 substrate in a complex. For example, compounds (e.g., 18232 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 18232 substrate) to interact with 18232 with or without the labeling of any of the interactants can be evaluated. For example, a microphysiometer can be used to detect the interaction of a compound with 18232 without the labeling of either the compound or 18232. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 18232.

In yet another embodiment, a cell-free assay is provided in which a 18232 protein or biologically active portion thereof is contacted with a test compound and the ability of the test compound to bind to the 18232 protein or biologically active portion thereof is evaluated. Preferred biologically active portions of the 18232 proteins to be used in assays of the present invention include fragments that participate in interactions with non-18232 molecules, e.g., fragments with high surface probability scores.

Soluble and/or membrane-bound forms of isolated proteins (e.g., 18232 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylaminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

Assay where ability of agent to block binding of the phosphatase to the phosphorylated substrate within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 18232 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound (which is not anchored), can be labeled, either directly or indirectly, with detectable labels discussed herein.

It may be desirable to immobilize either 18232, an anti 18232 antibody or its target molecule to facilitate separation of complexed from uncomplexed forms of one or both of the proteins, as well as to accommodate automation of the assay. Binding of a test compound to a 18232 protein, or interaction of a 18232 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/18232 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 18232 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 18232 binding or activity determined using standard techniques.

Other techniques for immobilizing either a 18232 protein or a target molecule on matrices include using conjugation of biotin and streptavidin. Biotinylated 18232 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 18232 protein or target molecules but which do not interfere with binding of the 18232 protein to its target molecule. Such antibodies can be derivatized to the wells of the plate, and unbound target or 18232 protein is trapped in the wells by antibody conjugation. Methods for detecting such complexes, in addition to those described above for the GST-immobilized complexes, include immunodetection of complexes using antibodies reactive with the 18232 protein or target molecule, as well as enzyme-linked assays which rely on detecting an enzymatic activity associated with the 18232 protein or target molecule.

Alternatively, cell free assays can be conducted in a liquid phase. In such an assay, the reaction products are separated from unreacted components by any of a number of standard techniques, including but not limited to: differential centrifugation (see, for example, Rivas, G., and Minton, A. P., (1993) *Trends Biochem Sci Aug;* 18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., (1998) *J Mol Recognit Winter,* 11(1–6):141–8; Hage, D. S., and Tweed, S. A. (1997) *J Chromatogr B Biomed Sci Appl* Oct 10;699(1–2) :499–525). Further, fluorescence energy transfer may also be conveniently utilized, as described herein, to detect binding without further purification of the complex from solution.

In a preferred embodiment, the assay includes contacting the 18232 protein or biologically active portion thereof with a known compound which binds 18232 to form an assay mixture, contacting the assay mixture with a test compound, and determining the ability of the test compound to interact with a 18232 protein, wherein determining the ability of the test compound to interact with a 18232 protein includes determining the ability of the test compound to preferentially bind to 18232 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/ products for use in this embodiment are the 18232 genes herein identified. In an alternative embodiment, the invention provides methods for determining the ability of the test compound to modulate the activity of a 18232 protein through modulation of the activity of a downstream effector of a 18232 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partners, is anchored onto a solid surface (e.g., a microtiter plate), while the non-anchored species is labeled either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes that have formed remain immobilized on the solid surface. In assays where the non-immobilized species is pre-labeled, the detection of label immobilized on the surface indicates that complexes were formed. In assays where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid-phase in the presence or absence of the test compound. Reaction products are separated from unreacted components and complexes detected using, for example, an immobilized antibody specific for one of the binding components to anchor any complexes formed in solution and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. For example, a preformed complex of the target gene product and the interactive cellular or extracellular binding partner product is prepared in which either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 18232 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 18232 ("18232-binding proteins" or "18232-bp") and are involved in 18232 activity. Such 18232-bps can be activators or inhibitors of signals by the 18232 proteins or 18232 targets as, for example, downstream elements of a 18232-mediated signaling pathway.

The two-hybrid system is based on the modular nature of most transcription factors, which consist of separable DNA-binding and activation domains. Briefly, the assay utilizes two different DNA constructs. In one construct, the gene that codes for a 18232 protein is fused to a gene encoding the DNA binding domain of a known transcription factor (e.g., GAL-4). In the other construct, a DNA sequence from a library of DNA sequences that encodes an unidentified protein ("prey" or "sample") is fused to a gene that codes for the activation domain of the known transcription factor. (Alternatively the 18232 protein can be fused to the activator domain.) If the "bait" and the "prey" proteins are able to interact in vivo and form a 18232-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 18232 protein.

In another embodiment, modulators of 18232 expression are identified. For example, a cell or cell free mixture is contacted with a candidate compound and the expression of 18232 mRNA or protein evaluated relative to the level of expression of 18232 mRNA or protein in the absence of the candidate compound. When expression of 18232 mRNA or protein is greater in the presence of the candidate compound than in its absence, the candidate compound is identified as a stimulator of 18232 mRNA or protein expression. Alternatively, when expression of 18232 mRNA or protein is less (statistically significantly less) in the presence of the candidate compound than in its absence, the candidate compound is identified as an inhibitor of 18232 mRNA or protein expression. The level of 18232 mRNA or protein expression can be determined by methods described herein for detecting 18232 mRNA or protein.

In another aspect, the invention pertains to a combination of two or more of the assays described herein. For example, a modulating agent can be identified using a cell-based or a cell free assay, and the ability of the agent to modulate the activity of a 18232 protein can be confirmed in vivo, e.g., in an animal such as an animal model overexpressing an oncogene encoding a protein tyrosine kinase.

This invention further pertains to novel agents identified by the above-described screening assays. Accordingly, it is within the scope of this invention to further use an agent identified as described herein (e.g., a 18232 modulating agent, an antisense 18232 nucleic acid molecule, a 18232-specific antibody, or a 18232-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 18232 with a disease; (ii) identify an individual from a minute biological sample (tissue typing); and (iii) aid in forensic identification of a biological sample. These applications are described in the subsections below.

Chromosome Mapping

The 18232 nucleotide sequences or portions thereof can be used to map the location of the 18232 genes on a chromosome. This process is called chromosome mapping. Chromosome mapping is useful in correlating the 18232 sequences with genes associated with disease.

Briefly, 18232 genes can be mapped to chromosomes by preparing PCR primers (preferably 15–25 bp in length) from the 18232 nucleotide sequences. These primers can then be used for PCR screening of somatic cell hybrids containing individual human chromosomes. Only those hybrids containing the human gene corresponding to the 18232 sequences will yield an amplified fragment.

A panel of somatic cell hybrids in which each cell line contains either a single human chromosome or a small number of human chromosomes and a full set of mouse chromosomes, allows easy mapping of individual genes to specific human chromosomes. (D'Eustachio P, et al. (1983) Science 220:919–924).

Other mapping strategies e.g., in situ hybridization (described in Fan, Y. et al. (1990) Proc. Natl. Acad. Sci. USA, 87:6223–27), pre-screening with labeled flow-sorted chromosomes, and pre-selection by hybridization to chromosome specific cDNA libraries can be used to map 18232 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the 18232 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 18232 sequences can be used to identify individuals from biological samples using, e.g., restriction fragment length polymorphism (RFLP). In this technique, an individual's genomic DNA is digested with one or more restriction enzymes, the fragments separated, e.g., by electrophoresis and Southern blotted, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 18232 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers, which each yield a noncoding amplified sequence of 100 bases. If predicted coding sequences, such as those in SEQ ID NO:3 are used, a more appropriate number of primers for positive individual identification would be 500–2,000.

If a panel of reagents from 18232 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 18232 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen, found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 and having a length of at least 20 bases, preferably at least 30 bases) are particularly appropriate for this use.

The 18232 nucleotide sequences described herein can further be used to provide polynucleotide reagents, e.g., labeled or labelable probes which can be used in, for example, an in situ hybridization technique, to identify a specific tissue, e.g., a tissue containing 18232 phosphatase activity. This can be very useful in cases where a forensic pathologist is presented with a tissue of unknown origin. Panels of such 18232 probes can be used to identify tissue by species and/or by organ type.

In a similar fashion, these reagents, e.g., 18232 primers or probes can be used to screen tissue culture for contamination (i.e., screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene that encodes 18232. Such disorders include, e.g., a disorder associated with the misexpression of 18232.

The method includes one or more of the following:

detecting, in a tissue of the subject, the presence or absence of a mutation which affects the expression of the 18232 gene, or detecting the presence or absence of a mutation in a region which controls the expression of the gene, e.g., a mutation in the 5' control region;

detecting, in a tissue of the subject, the presence or absence of a mutation which alters the structure of the 18232 gene;

detecting, in a tissue of the subject, the misexpression of the 18232 gene at the mRNA level, e.g., detecting a non-wild type level of a mRNA;

detecting, in a tissue of the subject, the misexpression of the gene at the protein level, e.g., detecting a non-wild type level of a 18232 polypeptide.

In preferred embodiments the method includes: ascertaining the existence of at least one of: a deletion of one or more nucleotides from the 18232 gene; an insertion of one or more nucleotides into the gene, a point mutation, e.g., a substitution of one or more nucleotides of the gene, or a gross chromosomal rearrangement of the gene, e.g., a translocation, inversion, or deletion.

For example, detecting the genetic lesion can include: (i) providing a probe/primer including an oligonucleotide containing a region of nucleotide sequence that hybridizes to a sense or antisense sequence from SEQ ID NO:1 or 3, or naturally occurring mutants thereof or 5' or 3' flanking sequences naturally associated with the 18232 gene; (ii) exposing the probe/primer to nucleic acid of the tissue; and (iii) detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 18232 gene; the presence of a non-wild type splicing pattern of a messenger RNA transcript of the gene; or a non-wild type level of 18232.

Methods of the invention can be used prenatally or to determine if a subject's offspring will be at risk for a disorder.

In preferred embodiments the method includes determining the structure of a 18232 gene, an abnormal structure being indicative of risk for the disorder.

In preferred embodiments the method includes contacting a sample form the subject with an antibody to the 18232 protein or a nucleic acid, which hybridizes specifically with the gene. This and other embodiments are discussed below.

Diagnostic and Prognostic Assays

The presence, level, or absence of 18232 protein or nucleic acid in a biological sample can be evaluated by obtaining a biological sample from a test subject and contacting the biological sample with a compound or an agent capable of detecting 18232 protein or nucleic acid (e.g., mRNA, genomic DNA) that encodes 18232 protein such that the presence of 18232 protein or nucleic acid is detected in the biological sample. The term "biological sample" includes tissues, cells and biological fluids isolated from a subject, as well as tissues, cells and fluids present within a subject. A preferred biological sample is serum. The level of expression of the 18232 gene can be measured in a number of ways, including, but not limited to: measuring the mRNA encoded by the 18232 genes; measuring the amount of protein encoded by the 18232 genes; or measuring the activity of the protein encoded by the 18232 genes.

The level of mRNA corresponding to the 18232 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 18232 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 18232 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 18232 genes.

The level of mRNA in a sample that is encoded by a 18232 nucleic acid can be evaluated with nucleic acid amplification, e.g., by rtPCR (Mullis, 1987, U.S. Pat. No. 4,683,202), ligase chain reaction (Barany (1991) *Proc. Natl. Acad. Sci. USA* 88:189–193), self sustained sequence replication (Guatelli et al. (1990) *Proc. Natl. Acad Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 18232 gene being analyzed.

In another embodiment, the methods further contacting a control sample with a compound or agent capable of detecting 18232 mRNA, or genomic DNA, and comparing the presence of 18232 mRNA or genomic DNA in the control sample with the presence of 18232 mRNA or genomic DNA in the test sample.

A variety of methods can be used to determine the level of protein encoded by 18232. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 18232 protein in a biological sample in vitro as well as in vivo. In vitro techniques for detection of 18232 protein include enzyme linked immunosorbent assays (ELISAs), immunoprecipitations, immunofluorescence, enzyme immunoassays (EIA), radioimmunoassays (RIA), and Western blot analysis. In vivo techniques for detection of 18232 protein include introducing into a subject a labeled anti-18232 antibody. For example, the antibody can be labeled with a radioactive marker whose presence and location in a subject can be detected by standard imaging techniques.

In another embodiment, the methods further include contacting the control sample with a compound or agent capable of detecting 18232 protein, and comparing the presence of 18232 protein in the control sample with the presence of 18232 protein in the test sample.

The invention also includes kits for detecting the presence of 18232 in a biological sample. For example, the kit can include a compound or agent capable of detecting 18232 protein or mRNA in a biological sample; and a standard. The compound or agent can be packaged in a suitable container. The kit can further comprise instructions for using the kit to detect 18232 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 18232 expression or activity. As used herein, the term "unwanted" includes an unwanted phenomenon involved in a biological response such as pain or deregulated cell proliferation.

In one embodiment, a disease or disorder associated with aberrant or unwanted 18232 expression or activity is identified. A test sample is obtained from a subject and 18232 protein or nucleic acid (e.g., mRNA or genomic DNA) is evaluated, wherein the level, e.g., the presence or absence, of 18232 protein or nucleic acid is diagnostic for a subject having or at risk of developing a disease or disorder associated with aberrant or unwanted 18232 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 18232 expression or activity. For example, such methods can be used to determine whether a subject can be effectively treated with an agent for a cell proliferation disorder.

The methods of the invention can also be used to detect genetic alterations in a 18232 gene, thereby determining if a subject with the altered gene is at risk for a disorder characterized by misregulation in 18232 protein activity or nucleic acid expression, such as a proliferation disorder. In preferred embodiments, the methods include detecting, in a sample from the subject, the presence or absence of a genetic alteration characterized by at least one of an alteration affecting the integrity of a gene encoding a 18232 protein, or the mis-expression of the 18232 gene. For example, such genetic alterations can be detected by ascertaining the existence of at least one of 1) a deletion of one or more nucleotides from a 18232 gene; 2) an addition of one or more nucleotides to a 18232 gene; 3) substitution of one or more nucleotides in a 18232 gene, 4) a chromosomal rearrangement of a 18232 gene; 5) an alteration in the level of a messenger RNA transcript of a 18232 gene, 6) aberrant modification of a 18232 gene, such as of the methylation pattern of the genomic DNA, 7) the presence of a non-wild type splicing pattern of a messenger RNA transcript of a 18232 gene, 8) a non-wild type level of a 18232-protein, 9) allelic loss of a 18232 gene, and 10) inappropriate post-translational modification of a 18232-protein.

An alteration can be detected with a probe/primer in a polymerase chain reaction, such as anchor PCR or RACE PCR, or, alternatively, in a ligation chain reaction (LCR), the latter of which can be particularly useful for detecting point mutations in the 18232-gene. This method can include the steps of collecting a sample of cells from a subject, isolating nucleic acid (e.g., genomic, mRNA or both) from the sample, contacting the nucleic acid sample with one or more primers that specifically hybridize to a 18232 gene under conditions such that hybridization and amplification of the 18232-gene (if present) occurs, and detecting the presence or absence of an amplification product or detecting the size of the amplification product and comparing the length to a control sample. It is anticipated that PCR and/or LCR may be desirable to use as a preliminary amplification step in conjunction with any of the techniques used for detecting mutations described herein. Alternative amplification methods are described above and can be used in a preliminary amplification step, followed by the detection of the amplified molecules using techniques known to those of skill in the art.

In another embodiment, mutations in a 18232 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicate mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 18232 can be identified by hybridizing sample and control nucleic acids, e.g., DNA or RNA, to two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 18232 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 18232 gene and detect mutations by comparing the sequence of the sample 18232 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 18232 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; and Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 18232 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 18232 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 18232 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments, amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 18232 gene.

Use of 18232 Molecules as Surrogate Markers

The 18232 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 18232 molecules of the invention may be detected, and may be correlated with one or more biological states in vivo. For example, the 18232 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) J. Mass. Spectrom. 35: 258–264; and James (1994) AIDS Treatment News Archive 209.

The 18232 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an 18232 marker) transcription or expression, the amplified marker may be in a quantity which is more readily detectable than the drug itself. Also, the marker may be more easily detected due to the nature of the marker itself; for example, using the methods described herein, anti-18232 antibodies may be employed in an immune-based detection system for an 18232 protein marker, or 18232-specific radiolabeled probes may be used to detect an 18232 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) Env. Health Perspect. 90: 229–238; Schentag (1999) Am. J. Health-Syst. Pharm. 56 Suppl. 3: S21–S24; and Nicolau (1999) Am, J. Health-Syst. Pharm. 56 Suppl. 3: S16–S20.

The 18232 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) Eur. J. Cancer 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 18232 protein or RNA) for specific tumor markers in a subject, a drug or course of treatment may be selected that is optimized for the treatment of the specific tumor likely to be present in the subject. Similarly, the presence or absence of a specific sequence mutation in 18232 DNA may correlate 18232 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-18232 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 μg/kg to about 500 mg/kg, about 100 μg/kg to about 5 mg/kg, or about 1 μg/kg to about 50 μg/kg. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 18232 expression or activity. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides. With regards to both prophylactic and therapeutic methods of treatment, such treatments may be specifically tailored or modified, based on knowledge obtained from the field of pharmacogenomic as described below.

In one aspect, the invention provides a method for preventing in a subject, a disease or condition associated with an aberrant or unwanted 18232 expression or activity, by administering to the subject 18232 or an agent that modulates 18232 expression or at least one 18232 activity. Subjects at risk for a disease that is caused or contributed to by aberrant or unwanted 18232 expression or activity can be identified by, for example, any or a combination of diagnostic or prognostic assays as described herein. Administration of a prophylactic agent can occur prior to the manifestation of symptoms characteristic of the 18232 aberrance, such that a disease or disorder is prevented or, alternatively, delayed in its progression. Depending on the type of 18232 aberrance, for example, a 18232 agonist or 18232 antagonist agent can be used for treating the subject. The appropriate agent can be determined based on screening assays described herein.

It is possible that some 18232 disorders can be caused, at least in part, by an abnormal level of gene product, or by the presence of a gene product exhibiting abnormal activity. As such, the reduction in the level and/or activity of such gene products would bring about the amelioration of disorder symptoms. In addition to hematopoietic disorders, 18232 disorders can include disorders of the lung, brain, heart, spinal cord, skeletal muscle, skin, and kidney, as well as non-neoplastic immune disorders.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schonlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

The 18232 nucleic acid and protein of the invention can be used to treat and/or diagnose a variety of non-neoplastic hematopoietic or immune disorders. Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders involving the brain include, but are limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrio-ventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the skeletal muscle include tumors such as rhabdomyosarcoma; hereditary myopathies, e.g., Duchenne muscular dystrophy, Becker muscular dystrophy, limb-girdle muscular dystrophy, congenital muscular dystrophy, myotonic dystrophy, facioscapulohumeral muscular dystrophy, and oculopharyngeal dystrophy; congenital myopathies, e.g., central core disease, nemaline myopathy, and centronuclear myopathy; muscular energy metabolic disorders, e.g., acid maltase deficiency, myophosphorylase deficiency, debranching enzyme deficiency, lactate dehydrogenase deficiency, etc.; muscular lipid metabolism disorders; e.g., myopathic carnitine deficiency, carnitine palmi-tyoltransferase deficiency, myodenylate deaminase deficiency; mitochondrial disorders, e.g., Kearns-Sayre syndrome, and myoclonic epilepsy and ragged red fibers syndrome; toxic myopathies; and periodic paralysis, e.g., hypokalemic periodic paralysis, hyperkalemic periodic paralysis, paramyotonia congenital, and thyrotoxic periodic paralysis.

As discussed above, successful treatment of 18232 disorders can be brought about by techniques that serve to inhibit the expression or activity of target gene products. For example, compounds, e.g., an agent identified using assays described above, that exhibits negative modulatory activities, can be used in accordance with the invention to prevent and/or ameliorate symptoms of 18232 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in which the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 18232 expression is through the use of aptamer molecules specific for 18232 protein. Aptamers are nucleic acid molecules having a tertiary structure that permits them to specifically bind to protein ligands (see, e.g., Osborne, et al. 1997 Curr. Opin. Chem Biol. 1(1): 5–9; and Patel, D. J. 1997 Curr Opin Chem Biol Jun;1(1):32–46). Since nucleic acid molecules may in many cases, be more conveniently introduced into target cells than therapeutic protein molecules, aptamers offer a method by which 18232 protein activity may be specifically decreased without the introduction of drugs or other molecules which may have pluripotent effects.

Antibodies can be generated that are both specific for target gene products and that reduce target gene product activity. Such antibodies may, therefore, by administered in instances whereby negative modulatory techniques are appropriate for the treatment of 18232 disorders. For a description of antibodies, see the Antibody section above.

In circumstances wherein injection of an animal or a human subject with a 18232 protein or epitope for stimulating antibody production is harmful to the subject, it is possible to generate an immune response against 18232 through the use of anti-idiotypic antibodies (see, for example, Herlyn, D. 1999 Ann Med 31(1):66–78; and Bhattacharya-Chatterjee, M., and Foon, K. A. 1998 Cancer Treat Res 94:51–68). If an anti-idiotypic antibody is introduced into a mammal or human subject, it should stimulate the production of anti-anti-idiotypic antibodies, which should be specific to the 18232 protein. Vaccines directed to a disease characterized by 18232 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) Proc. Natl. Acad. Sci. USA 90:7889–7893).

The identified compounds that inhibit target gene expression, synthesis and/or activity can be administered to a patient at therapeutically effective doses to prevent, treat or ameliorate 18232 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ and the $ED_{50}$ as described above in the Pharmaceutical Composition section.

Another example of determination of effective dose for an individual is the ability to directly assay levels of "free" and "bound" compound in the serum of the test subject. Such assays may utilize antibody mimics and/or "biosensors" that have been created through molecular imprinting techniques. A compound that is able to modulate 18232 activity is used as a template or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell, R. J. et al (1996) Current Opinion in Biotechnology 7:89–94 and in Shea, K. J. (1994) Trends in Polymer Science 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) Nature 361:645–647. Through the use of isotope-labeling, the "free" concentration of compound which modulates the expression or activity of 18232 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) Analytical Chemistry 67:2142–2144.

Another aspect of the invention pertains to methods of modulating 18232 expression or activity for therapeutic purposes. Accordingly, in an exemplary embodiment, the modulatory method of the invention involves contacting a cell with 18232 or agent that modulates one or more of the activities of 18232 protein activity associated with the cell. An agent that modulates 18232 protein activity can be an agent as described herein, such as a nucleic acid or a protein, a naturally-occurring target molecule of a 18232 protein (e.g., a 18232 substrate or receptor), a 18232 antibody, a 18232 agonist or antagonist, a peptidomimetic of a 18232 agonist or antagonist, or other small molecule.

In one embodiment, the agent stimulates one or more 18232 activities. Examples of such stimulatory agents include active 18232 protein and a nucleic acid molecule encoding 18232. In another embodiment, the agent inhibits one or more 18232 activities. Examples of such inhibitory agents include antisense 18232 nucleic acid molecules, anti-18232 antibodies, and 18232 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 18232 protein or nucleic acid molecule. In one embodiment, the method involves administering an agent (e.g., an agent identified by a screening assay described herein), or combination of agents that modulates (e.g., upregulates or downregulates) 18232 expression or activity. In another embodiment, the method involves administering a 18232 protein or nucleic acid molecule as therapy to compensate for reduced, aberrant, or unwanted 18232 expression or activity.

Stimulation of 18232 activity is desirable in situations in which 18232 is abnormally downregulated and/or in which increased 18232 activity is likely to have a beneficial effect. For example, stimulation of 18232 activity is desirable in situations in which a 18232 is downregulated and/or in which increased 18232 activity is likely to have a beneficial effect. Likewise, inhibition of 18232 activity is desirable in situations in which 18232 is abnormally upregulated and/or in which decreased 18232 activity is likely to have a beneficial effect.

Pharmacogenomics

The 18232 molecules of the present invention, as well as agents, or modulators which have a stimulatory or inhibitory effect on 18232 activity (e.g., 18232 gene expression) as identified by a screening assay described herein can be administered to individuals to treat (prophylactically or therapeutically) 18232-associated disorders associated with aberrant or unwanted 18232 activity (e.g., hyperproliferative disorders, e.g., cancer). In conjunction with such treatment, pharmacogenomics may be considered. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 18232 molecules of the present invention or 18232 modulators according to that individual's drug response genotype.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11):983–985 and Linder, M. W. et al. (1997) Clin. Chem. 43(2):254–266. In general, two types of pharmacogenomic conditions can be differentiated. Genetic conditions transmitted as a single factor altering the way drugs act on the body (altered drug action) or genetic conditions transmitted as single factors altering the way the body acts on drugs (altered drug metabolism). These pharmacogenomic conditions can occur either as rare genetic defects or as naturally-occurring polymorphisms.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 44576 molecule or 44576 modulator as well as tailoring the dosage and/or therapeutic regimen of treatment with a 44576 molecule or 44576 modulator.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 18232 protein of the present invention), all common variants of that gene can be fairly easily identified in the population and it can be determined if having one version of the gene versus another is associated with a particular drug response.

Alternatively, a method termed "gene expression profiling", can be utilized to identify genes that predict drug response. For example, the gene expression of an animal dosed with a drug (e.g., a 18232 molecule or 18232 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 18232 molecule or 18232 modulator, such as a modulator identified by one of the exemplary screening assays described herein.

The present invention further provides methods for identifying new agents, or combinations, that are based on identifying agents that modulate the activity of one or more of the gene products encoded by one or more of the 18232 genes of the present invention, wherein these products may be associated with resistance of the cells to a therapeutic agent. Specifically, the activity of the proteins encoded by the 18232 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 18232 protein can be applied in clinical trials. For example, the effectiveness of an agent determined by a screening assay as described herein to increase 18232 gene expression, protein levels, or upregulate 18232 activity, can be monitored in clinical trials of subjects exhibiting decreased 18232 gene expression, protein levels, or downregulated 18232 activity. Alternatively, the effectiveness of an agent determined by a screening assay to decrease 18232 gene expression, protein levels, or downregulate 18232 activity, can be monitored in clinical trials of subjects exhibiting increased 18232 gene expression, protein levels, or upregulated 18232 activity. In such clinical trials, the expression or activity of a 18232 gene, and preferably, other genes that have been implicated in, for example, a 18232-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 18232, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 18232 nucleic acid, polypeptide, or antibody.

The capture probes can be a set of nucleic acids from a selected sample, e.g., a sample of nucleic acids derived from a control or non-stimulated tissue or cell.

The method can include contacting the 18232 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes, each of which specifically hybridizes, with an allele of 18232. Such methods can be used to diagnose a subject, e.g., to evaluate risk for a disease or disorder, to evaluate suitability of a selected treatment for a subject, to evaluate whether a subject has a disease or disorder. 18232 is associated with regulation of cell growth and proliferation, thus it is useful for evaluating, e.g., proliferation disorders.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 18232 or from a cell or subject in which a 18232 mediated response has been elicited, e.g., by contact of the cell with 18232 nucleic acid or protein, or administration to the cell or subject 18232 nucleic acid or protein; contacting the array with one or more inquiry probes, wherein an inquiry probe can be a nucleic acid, polypeptide, or antibody (which is preferably other than 18232 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 18232 (or does not express as highly as in the case of the 18232 positive plurality of capture probes) or from a cell or subject which in which a 18232 mediated response has not been elicited (or has been elicited to a lesser extent than in the first sample); contacting the array with one or more inquiry probes (which is preferably other than a 18232 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing 18232, e.g., analyzing structure, function, or relatedness to other nucleic acid or amino acid sequences. The method includes: providing a 18232 nucleic acid or amino acid; comparing the 18232 sequence with one or more preferably a plurality of sequences from a collection of sequences, e.g., a nucleic acid or protein sequence database; to thereby analyze 18232. Preferred databases include GenBank. The method can include evaluating the sequence identity between a 18232 sequence and a database sequence. The method can be performed by accessing the database at a second site, e.g., over the internet.

In another aspect, the invention features, a set of oligonucleotides, useful, e.g., for identifying SNP's, or identifying specific alleles of 18232. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with differential labels, such that an oligonucleotide that hybridizes to one allele provides a signal that is distinguishable from an oligonucleotide that hybridizes to a second allele.

This invention is further illustrated by the following examples that should not be construed as limiting. The contents of all references, patents and published patent applications cited throughout this application are incorporated herein by reference.

EXAMPLES

Example 1
Identification and Characterization of Human 18232 cDNA

The human 18232 sequence (FIG. 1; SEQ ID NO:1), which is approximately 1390 nucleotides long including untranslated regions, contains a predicted methionine-initiated coding sequence of about 531 nucleotides (nucleotides 329 to 859 of SEQ ID NO:1; SEQ ID NO:3). The coding sequence encodes a 176 amino acid protein (SEQ ID NO:2).

Example 2
Tissue Distribution of 18232 mRNA

Endogenous human 18232 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 18232 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from 1 $\mu$g total RNA using an oligo-dT primer and Superscript II reverse transcriptase (Gibco/BRL). cDNA obtained from approximately 50 ng total RNA was used per TaqMan reaction.

18232 mRNA levels were analyzed in a variety of samples of isolated and/or treated hematopoietic cells, in particular, hematopoietic progenitor CD34 cells. Expression was then further restricted primarily to the erythroid lineage and increases as bone marrow/blood cell differentiation proceeds.

Figure 5:
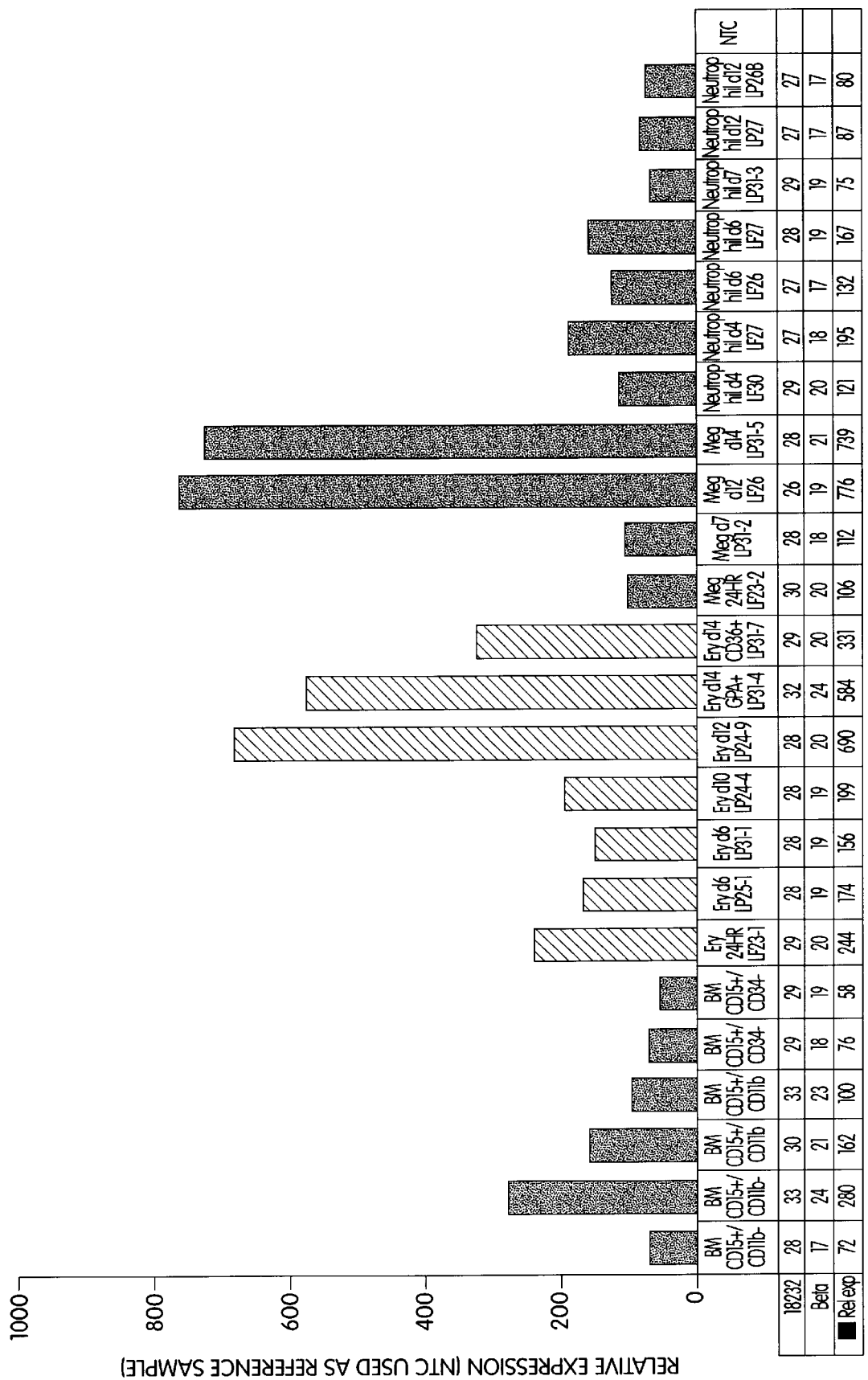
FIG. 5 is a bar graph depicting relative 18232 mRNA expression as determined by TaqMan assays on mRNA derived from human hematological samples, e.g., bone marrow (BM), erythroid cells (ery), megakaryocytes (meg), neutrophils, and a negative reference sample (NTC). In some samples, mRNA expression was detected at the indicated times in culture (e.g., 24 hrs., 48 hrs., days in culture). High levels of 18232 mRNA expression, i.e., greater than 200 relative units, were observed in one sample of CD15+, Cd11B-bone marrow; in erythroid cells, especially day 14 erythroid cells, glycophorin A or CD36+ erythroid cells; and in day 12 and day 14 megakaryocytes.

High levels of 18232 mRNA expression, i.e., greater than 200 relative units, was observed in skeletal muscle, fetal liver, and bone marrow with low GPA levels (FIG. 4), and in late stage erythroid cells (Ery d10, d12) (FIG. 5). Moderate to high level mRNA expression, i.e., greater than 100 relative units, was observed in lung tissue, in differentiating erythroid cells, and in CD36+ erythroid cells (d14) (FIG. 5).

FIG. 5 shows relative 18232 mRNA expression on mRNA derived from human hematological samples, e.g., bone marrow (BM), erythroid cells (ery), megakaryocytes (meg), neutrophils, and a negative reference sample (NTC). In some samples, mRNA expression was detected at the indicated times in culture (e.g., 24 hrs., 48 hrs., days in culture). High levels of 18232 mRNA expression, i.e., greater than 200 relative units, were observed in one sample of CD15+, Cd11B-bone marrow; in erythroid cells, especially day 14 erythroid cells, glycophorin A or CD36+ erythroid cells; and in day 12 and day 14 megakaryocytes.

Figure 6:
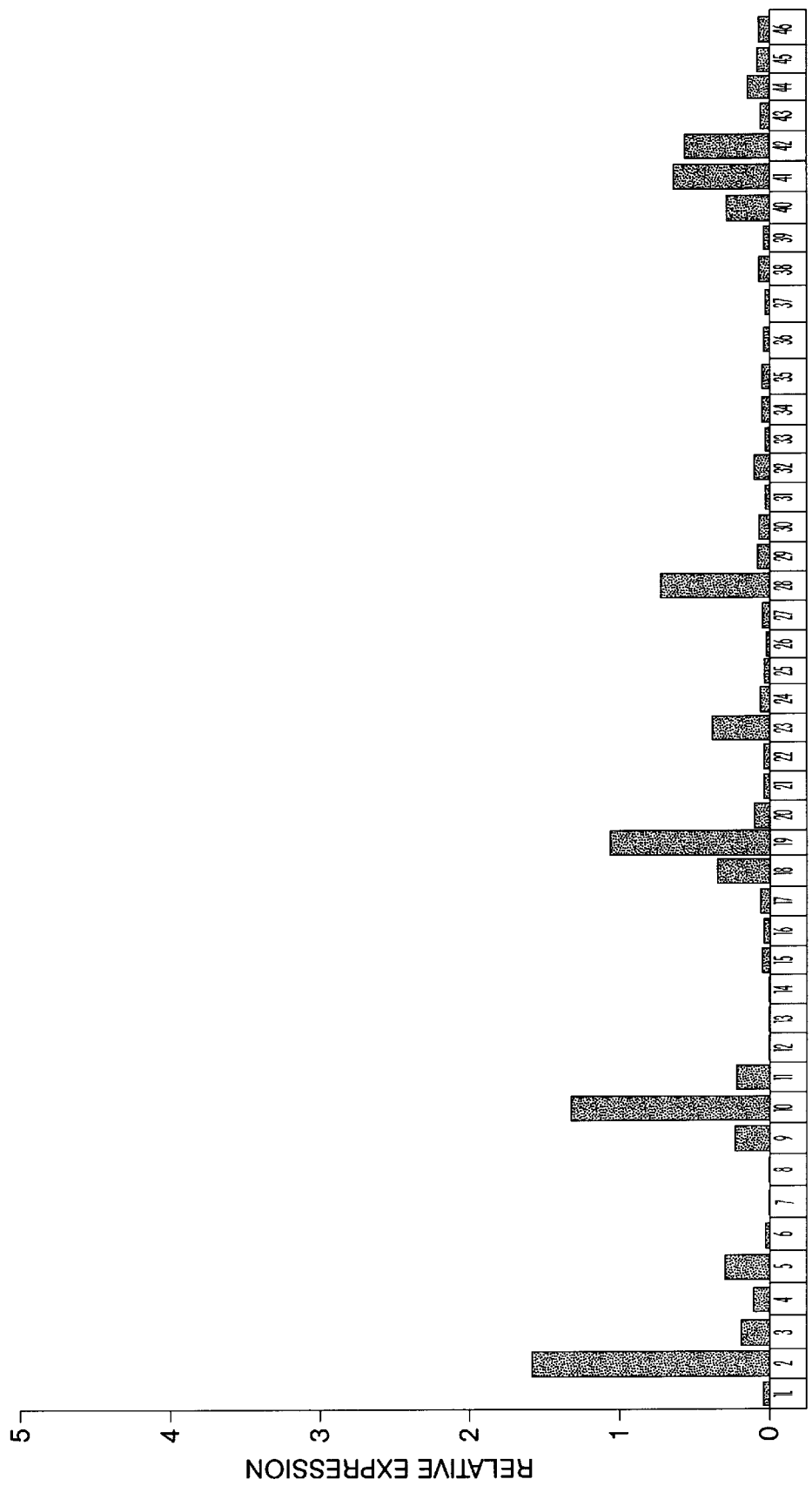
FIG. 6 is a bar graph depicting relative 18232 mRNA expression as determined by TaqMan assays on mRNA derived from human tissue samples, both normal and tumor. The samples are derived from the following tissues, with the relative expression level shown in parentheses: 1) normal colon (0.035); 2) epithelial cells (1.566); 3–5) colon tumors (0.184, 0.108, and 0.300, respectively); 6–8) colon tumors 18D—WUM3, 4, and 6 (0.012, 0.002, and 0.007, respectively); 9–11) normal kidney (0.229, 1.320, and 0.222, respectively); 12–14) normal liver (0.002, 0.004, and 0.002, respectively); 15–17) liver fibroses (0.041, 0.024, and 0.054, respectively); 18–19) fetal liver (0.038 and 1.054, respectively); 20–22) normal lung (0.086, 0.021, and 0.017, respectively); 23–24) lung tumors (0.366 and 0.050, respectively); 25–28) lung samples characterized by chronic obstructive pulmonary disease (0.0210.006, 0.040, and 0.712, respectively); 29–31) normal spleen (0.059, 0.059, and 0.009, respectively); 32–34) normal tonsils (0.043, 0.001, and 0.019, respectively); 35–37) normal lymph nodes (0.029, 0.014, and 0.005, respectively); 38) normal thymus (0.049); 39) endothelial cells (0.012); 40–42) skeletal muscle (0.285, 0.642, and 0.569, respectively); 43) fibroblasts (0.048); 44–46) normal skin (0.131, 0.068, and 0.063, respectively). The highest relative expression among these samples was found in epithelial cells, kidney, fetal liver, lung, and skeletal muscle.

FIG. 6 shows relative 18232 mRNA expression on mRNA derived from human tissue samples, both normal, and tumor. The samples are derived from epithelial cells, colon, kidney, liver, fetal liver, lung, spleen, tonsil, lymph node, thymus, endothelial cells, skeletal muscle, fibroblast, and skin. The highest relative expression among these samples was found in epithelial cells, kidney, fetal liver, lung, and skeletal muscle.

Figure 7:
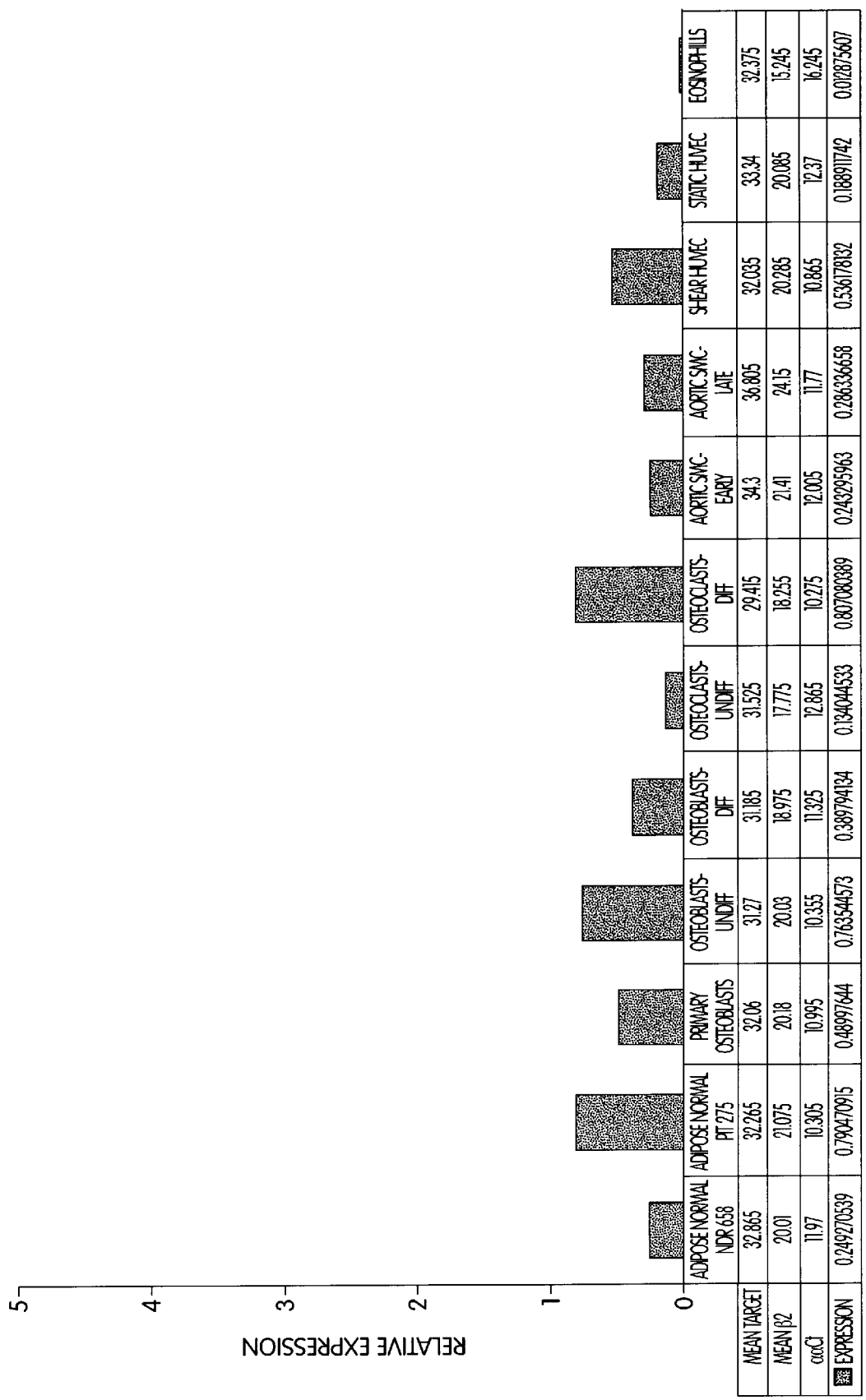
FIG. 7 is a bar graph depicting relative 18232 mRNA expression as determined by TaqMan assays on mRNA derived from adipose tissue, osteoblasts, aortic smooth muscle cells, and human umbilical vein endothelial cells (HUVEC).
Figure 8:
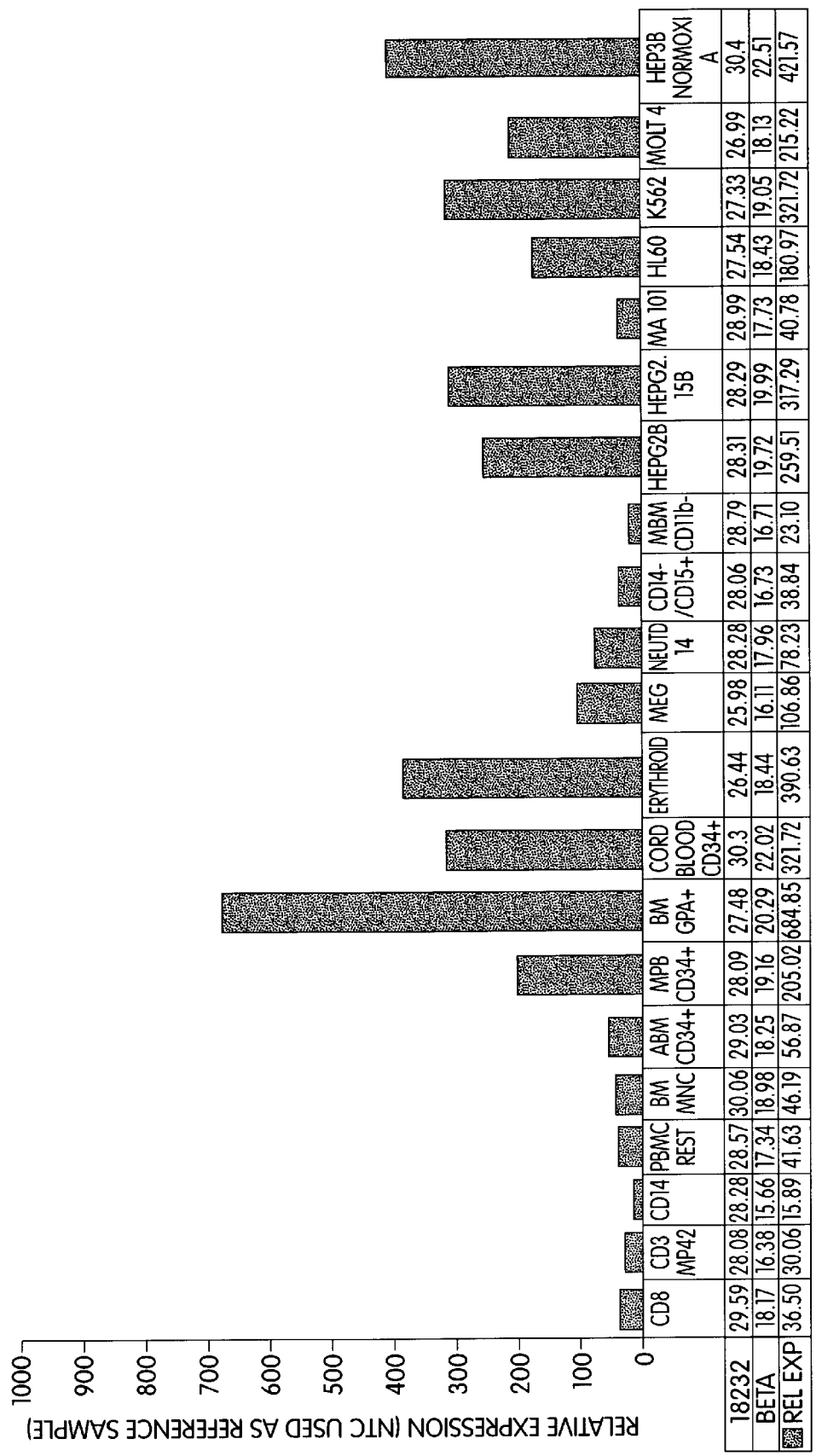
FIG. 8 is a bar graph depicted relative 18232 mRNA expression as determined by TaqMan assays on mRNA derived from hematopoietic cells, including CD8+ cells, CD3+ cells, CD14+ cells, peripheral blood cells, bone marrow cells, cord blood cells, and cells from cell culture lines, e.g., HepG2B, MA101, HL60, K562, Molt4, and Hep3B cells. High 18232 expression was observed in glycophorin A positive bone marrow cells.

FIG. 7 shows relative 18232 mRNA expression on mRNA derived from adipose tissue, osteoblasts, aortic smooth muscle cells, and human umbilical vein endothelial cells (HUVEC). FIG. 8 shows relative 18232 mRNA expression in a variety of blood cells, e.g., CD8 positive cells, bone marrow cells, and cell culture lines (e.g., HepG2B, MA101, HL60, K562, and Hep3B).

Northern blot hybridizations with various RNA samples can be performed under standard conditions and washed under stringent conditions, i.e., 0.2×SSC at 65° C. A DNA probe corresponding to all or a portion of the 18232 cDNA (SEQ ID NO:1) can be used. The DNA can be radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3
Recombinant Expression of 18232 in Bacterial Cells

In this example, 18232 is expressed as a recombinant glutathione-S-transferase (GST) fusion polypeptide in *E.*

*coli* and the fusion polypeptide is isolated and characterized. Specifically, 18232 is fused to GST and this fusion polypeptide is expressed in *E. coli*, e.g., strain PEB199. Expression of the GST-18232 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4
Expression of Recombinant 18232 Protein in COS Cells

To express the 18232 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 18232 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 18232 DNA sequence is amplified by PCR using two primers. The 5' primer contains the restriction site of interest followed by approximately twenty nucleotides of the 18232 coding sequence starting from the initiation codon; the 3' end sequence contains complementary sequences to the other restriction site of interest, a translation stop codon, the HA tag or FLAG tag and the last 20 nucleotides of the 18232 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 18232 gene is inserted in the correct orientation. The ligation mixture is transformed into *E. coli* cells (strains HB 101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 18232-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the 18232 polypeptide is detected by radiolabeling ($^{35}$S-methionine or $^{35}$S-cysteine available from NEN, Boston, Mass., can be used) and immunoprecipitation (Harlow, E. and Lane, D. Antibodies. A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 18232 coding sequence is cloned directly into the polylinker of the pCDNA/Amp vector using the appropriate restriction sites. The resulting plasmid is transfected into COS cells in the manner described above, and the expression of the 18232 polypeptide is detected by radiolabelling and immunoprecipitation using a 18232 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:

a) a nucleic acid molecule comprising the nucleotide sequence of SEQ ID NO:1 or a full complement thereof;

b) a nucleic acid molecule comprising a fragment of the nucleotide sequence of SEQ ID NO:1, wherein the fragment is at least 550 nucleotides in length and encodes a protein having dual specificity phosphatase activity, or a full complement thereof;

c) a nucleic acid molecule consisting of the nucleotide sequence of SEQ ID NO:3, or a full complement thereof;

d) a nucleic acid molecule consisting of the nucleotide sequence of SEQ ID NO:3 and a heterologous nucleic acid sequence, wherein the heterologous nucleic acid sequence is a heterologous regulatory sequence, or a full complement thereof;

d) a nucleic acid molecule consisting of the nucleotide sequence of SEQ ID NO:3 and a heterologous nucleic acid sequence, wherein the heterologous nucleic acid sequence is a heterologous regulatory sequence, or a full complement thereof;

e) a nucleic acid molecule which encodes a polypeptide consisting of the amino acid sequence of SEQ ID NO:2, or a full complement thereof;

f) a nucleic acid molecule which encodes a polypeptide consisting of a fragment of the amino acid sequence of SEQ ID NO:2, wherein the fragment is selected from the group consisting of amino acid residues 1–156, 18–176, and 18–156 of SEQ ID NO:2, or a full complement thereof;

g) a nucleic acid molecule which encodes a polypeptide consisting of the amino acid sequence of SEQ ID NO:2 and a heterologous polypeptide sequence, or a full complement thereof; and h) a nucleic acid molecule which encodes a polypeptide consisting of a fragment of the amino acid sequence of SEQ ID NO:2 and a heterologous polypeptide sequence, wherein the fragment is selected from the group consisting of amino acid residues 1–156, 18–176, and 18–156 of SEQ ID NO:2, or a full complement thereof.

2. The nucleic acid molecule of claim 1 further comprising vector nucleic acid sequences.

3. The nucleic acid molecule of claim 1 further comprising nucleic acid sequences encoding a heterologous polypeptide.

4. A host cell which contains the nucleic acid molecule of claim 1.

5. The host cell of claim 4 which is a mammalian host cell.

6. A non-human mammalian host cell containing the nucleic acid molecule of claim 1.

7. A method for producing a polypeptide comprising the amino acid sequence of SEQ ID NO:2 comprising culturing the host cell of claim 4 under conditions in which the nucleic acid molecule is expressed.

8. The nucleic acid molecule of claim 1, which comprises the nucleotide sequence of SEQ ID NO:1 or a full complement thereof.

9. The nucleic acid molecule of claim 1, which consists of the nucleotide sequence of SEQ ID NO:3 or a full complement thereof.

10. The nucleic acid molecule of claim 1, which encodes a polypeptide consisting of the amino acid sequence of SEQ ID NO:2, or a full complement thereof.

11. The nucleic acid molecule or claim 1, which comprises a fragment of the nucleotide sequence of SEQ ID NO:1, wherein the fragment is at least 550 nucleotides in length and encodes a protein having dual specificity phosphatase activity, or a full complement thereof.

12. The nucleic acid molecule of claim 1, which consists of the nucleotide sequence of SEQ ID NO:3 and a heterologous nucleic acid sequence, wherein the heterologous nucleic acid sequence is a heterologous regulatory sequence, or a full complement thereof.

13. The nucleic acid molecule of claim 1, which encodes a polypeptide consisting of a fragment of the amino acid sequence of SEQ ID NO:2, wherein the fragment is selected from the group consisting of amino acid residues 1–156, 18–176, and 18–156 of SEQ ID NO:2, or a full complement thereof.

14. The nucleic acid molecule of claim 1, which encodes a polypeptide consisting of the amino acid sequence of SEQ ID NO:2 and a heterologous polypeptide sequence, or a full complement thereof.

15. The nucleic acid molecule of claim 1, which encodes a polypeptide consisting of a fragment of the amino acid sequence of SEQ ID NO:2 and a heterologous polypeptide sequence, wherein the fragment is selected from the group consisting of amino acid residues 1–156, 18–176, and 18–156 of SEQ ID NO:2, or a full complement thereof.

* * * * *